United States Patent [19]

Maeda et al.

[11] Patent Number: 5,593,861
[45] Date of Patent: Jan. 14, 1997

[54] DOG-MOUSE HETEROHYBRIDOMA AND GENE FRAGMENT CODING FOR CONSTANT REGION OF CANINE IMMUNOGLOBULINS

[75] Inventors: Hiroaki Maeda, Kumamoto; Yasuyuki Eda, Koshi-machi; Kazuhiko Kimachi, Kumamoto; Yoichi Ono, Kumamoto; Sachio Tokiyoshi, Kumamoto, all of Japan

[73] Assignee: Juridical Foundation The Chemo-Sero-Therapeutic Research Institute, Kumamoto-ken, Japan

[21] Appl. No.: 306,520

[22] Filed: Sep. 15, 1994

Related U.S. Application Data

[63] Continuation of Ser. No. 46,903, Apr. 15, 1993, abandoned, which is a continuation of Ser. No. 571,215, Aug. 23, 1990, abandoned.

[30] Foreign Application Priority Data

Aug. 25, 1989 [JP] Japan .................................... 1-219889
Sep. 30, 1989 [JP] Japan .................................... 1-255425
Jun. 7, 1990 [JP] Japan .................................... 2-150673

[51] Int. Cl.$^6$ ........................... C12N 15/00; C07H 21/04; C12P 21/06; C12P 21/04
[52] U.S. Cl. ................... 435/69.1; 435/69.6; 435/172.3; 435/320.1; 536/23.53; 536/23.1
[58] Field of Search ................................ 435/69.6, 69.1, 435/320.1, 172.3; 536/23.53

[56] References Cited

U.S. PATENT DOCUMENTS 4,842,999  6/1989  Fuller et al. ................................ 435/7

FOREIGN PATENT DOCUMENTS 0289053  11/1988  European Pat. Off. .

OTHER PUBLICATIONS

Bio Essays, vol. 8, No. 2, Feb./Mar. 1988, pp. 74–78; M. Verhoeyen et al. "Engineering of Antibodies".

Clinical Chemistry, vo. 34, No. 9, 1988, pp. 1668–1675; S. L. Morrison et al. "Production and characterization of genetically engineered antibody molecules".

Wasserman et al Biochemistry 16(14):3161, 1977.

Morrison et al Clin Chem 34(9):1668. 1988.

Fuller et al Fed. Proceedings 44(4): 1329. 1985 (Abst #5369).

Wasserman et al 16(14): 3160, 1977.

*Primary Examiner*—Suzanne E. Ziska
*Attorney, Agent, or Firm*—Birch, Stewart, Kolasch & Birch, LLP

[57] ABSTRACT

A gene fragment which comprises a DNA sequence coding for an amino acid sequence of a constant region of canine immunoglobulin lambda chain; a gene fragment which comprises a DNA sequence coding for an amino acid sequence of a constant region of canine immunoglobulin kappa chain; a gene fragment which comprises a DNA sequence coding for the constant region of canine immunoglobulin gamma chain; a recombinant DNA molecule coding for an amino acid sequence of a mouse-dog chimeric antibody which comprises a gene fragment coding for an amino acid sequence of a variable region of a mouse immunoglobulin and a gene fragment coding for an amino acid sequence of a constant region of a canine immunoglobulin; a polypeptide of a mouse-dog chimeric antibody which is expressed from a cell transformed with an expression vector for cells wherein said recombinant DNA molecule cording for an amino acid sequence of the mouse-dog chimeric antibody is incorporated; a dog-mouse heterohybridoma which produces canine immunoglobulin; and a process for preparing a canine immunoglobulin gene.

6 Claims, 20 Drawing Sheets

CAGCCCAAGG CCTCCCCCTC GGTCACACTC TTCCCGCCCT CCTCTGAGGA GCTCGGCGCC
AACAAGGCCA CCCTGGTGTG CCTCATCAGC GACTTCTACC CCAGCGGCGT GACGGTGGCC
TGGAAGGCAA GCGGCAGCCC CGTCACCCAG GGCGTGGAGA CCACCAAGCC CTCCAAGCAG
CACAGCAGCT TCAGCTGCCT GGTCACGCAC GAGGGGAGCA CCGTGGAGAA GAAGGTGGCC
CCCGCAGAGT GCTCTTAG

FIG. 6

GlnProLysAlaSerProSerValThrLeuPheProProSerSerGluGluLeuGlyAla
AsnLysAlaThrLeuValCysLeuIleSerAspPheTyrProSerGlyValThrValAla
TrpLysAlaSerGlySerProValThrGlnGlyValGluThrThrLysProSerLysGln
SerAsnAsnLysTyrAlaAlaSerSerTyrLeuSerLeuThrProAspLysTrpLysSer
HisSerSerPheSerCysLeuValThrHisGluGlySerThrValGluLysLysValAla
ProAlaGluCysSer

FIG. 7

AATGATGCCC AGCCAGCCGT CTATTTGTTC CAACCATCTC CAGACCAGTT ACACACAGGA
AGTGCCTCTG TTGTGTGTTT GCTGAATAGC TTCTACCCCA AAGACATCAA TGTCAAGTGG
AAAGTGGATG GTGTCATCCA AGACACAGGC ATCCAGGAAA GTGTCACAGA GCAGGACAAG
GACAGTACCT ACAGCCTCAG CAGCACCCTG ACGATGTCCA GTACTGAGTA CCTAAGTCAT
GAGTTGTACT CCTGTGAGAT CACTCACAAG AGCCTGCCCT CCACCCTCAT CAAGAGCTTC
CAAAGGAGCG AGTGTCAGAG AGTGGACTAA

FIG. 11

AsnAspAlaGlnProAlaValTyrLeuPheGlnProSerProAspGlnLeuHisThrGly
SerAlaSerValValCysLeuLeuAsnSerPheTyrProLysAspIleAsnValLysTrp
LysValAspGlyValIleGlnAspThrGlyIleGlnGluSerValThrGluGlnAspLys
AspSerThrTyrSerLeuSerSerThrLeuThrMetSerSerThrGluTyrLeuSerHis
GluLeuTyrSerCysGluIleThrHisLysSerLeuProSerThrLeuIleLysSerPhe
GlnArgSerGluCysGlnArgValAsp

FIG. 12

```
TCTTGCAGCC TCCACCACGG CCCCCTCGGT TTTCCCACTG GACCCCAGCT GCGGGTCCAC

TTCCGGCTCC ACGGTGGCCC TGGCCTGCCT GGTGTCAGGC TACTTCCCCG AGCCTGTAAC

TGTGTCCTGG AATTCCGGCT CCTTGACCAG CGGTGTGCAC ACCTTCCCGT CCGACCTGCA

GTCCTCAGGG CTCTACTCCC TCAGCAGCAT GGTGACAGTG CCCTCCAGCA GGTGGTCCAG

CGAGACCTTC ACCTGCAACG TGGCCCACCC GGCCAGCAAA ACTAAAGTAG ACAAGCCAGG

TGAGACGTCG GACTCAGAGA GGGGTCCACT CGGGACAAGC CAGATCAGCT GTCCCTCCCA

GACCCACGTC ACCGGGGAGT CACCTCAGTG TCCCCGTCCT CAAGGCCTCC CCTTTCTGGG

AAGGTGTCCT CTGGGCGTGG CTGCCTGGTC CAGATGACCA CAGGCTGCAT TCCCCACTGT

ATTCCCAGGA CCCATTGGTG CCACTGCTCG AGGGTCCCTA AGTCACCCAA GACCTGTGCC

ACACCAGGGG GAGTAACCCC CAGTCTGCTC TCTCTGCATT GCCCAAAAGA GAAAATGGAA

GAGTTCCTCG CCCACCTGAT TGTCCCAAAT GCCCAGGTGA GTCAGCAGGG CCCTGCTCTG

CATCCCAAGC CGATGGTGCA CACCCAGGCA CAGCCTGATG GGCTAATGGG TGTTGGAGAA

GTCCACCGAA GTGCTACCTC ATCCTTGTGT CTTCCATTTT AGCCCCTGAA ATGCTGGGAG

GGCCTTCGGT CTTCATCTTT CCCCCGAAAC CCAAGGACAC CCTCTTGATT GCCCGAACAC

CTGAGGTCAC ATGTGTGGTG GTGGATCTGG GACCAGAAGA CCCTGAGGTG CAGATCAGCT

GGTTCGTGGA CGGTAAGCAG ATGCAAACAG CCAAGACTCA GCCTCGTGAG GAGCAGTTCA

ATGGCACCTA CCGTGTGGTC AGTGTCCTCC CCATTGGGCA CCAGGACTGG CTCAAGGGGA

AGCAGTTCAC GTGCAAAGTC AACAACAAAG CCCTCCCATC CCCGATCGAG AGGACCATCT

CCAAGGCCAG AGGTAGGCAG CAGGGCATAG GGGATGCAGG GAGGGAGAGT TGCCTGTAAA

TTGATACCAG TCCTCCACCC TGATAGTGAC CATCTGTGCT GATCCTTTAC CCCATAGGGC

AGGCCCATCA GCCCAGTGTG TATGTCCTGC CGCCATCCCG GGAGGAGTTG AGCAAGAACA
```

FIG. 16A

```
CAGTCAGCTT GACATGCCTG ATCAAAGACT TCTTCCCACC TGACATTGAT GTGGAGTGGC

AGAGCAATGG ACAGCAGGAG CCTGAGAGCA AGTACCGCAC GACCCCGCCC CAGCTGGACG

AGGACGGGTC CTACTTCCTG TACAGCAAGC TCTCTGTGGA CAAGAGCCGC TGGCAGCGGG

GAGACACCTT CATATGTGCG GTGATGCATG AAGCTCTACA CAACCACTAC ACACAGAAAT

CCCTCTCCCA TTCTCCGGGT AAATGAGCAA CACGCCCGGC ACCCAGCAAG CCCCCCACCC

TTGGCTCTCA GGATCCCCGG GTACCGAGCT C
```

FIG. 16B

CTGAGCCTGG GGGTCTCACA GCCTCCTCTC TTGCAGCCTC CTCCACGGCC CCCTCAGTTT

TCCCACTGGC CCCCAGCTGC GGGTCCACTT CCGGCTCCAC GGTGACCCTG GCCTGCCTGG

TGTCAGGCTA CTTCCCCGAG CCTGTAACTG TGTCCTGGAA TTCCGGCTCC TTGACCAGCG

GTGTGCACAC CTTCCCGTCC GTCCTGAAGT CCTCAGGGCT CTACTCCCTC AGCAGCATGG

TGACAGTGCC CTCCAGCAGG TTGCCCAGCG AGACCTTCAC CTGCAACGTG GTCCACCCGG

CCACCAACAC TAAAGTAGAC AAGCCAGGTG AGACGTCAGA CTCAGAGAGG GGTCAGCTCA

GGACAGGCCA AATCAGCTGT CTCTCCGGAC CCATGGCACC GGGGAATCAC CTCAGTGTCC

CCGTCCTCAA GGCCTCCCCT TTCTGGGAAG GTGTCCTCTG GGCGTGGCTG CCTGGTCCAG

ATGACCACAA GCTGCATTCC CCACTGCATT CCTGGGTCCA TTGGGTGCCA CTGGTCGGGG

ATCCCCTCAT GAGCTGGCCT GACCTAAGTT CACCCCATGA CCTGTGCCCA CCCCAGGCCC

CCAATAACCC CTAGTCTGCT CTCTCTGCAG TGCCCAAAGA GTCCACCTGC AAGTGTATAT

CCCCATGCCC AGGTGAGTCA GCAGGGCCCT GCTCTGCACC CCAAGCAGAT GTTGCACATC

CAGGCACAGA CTAATGGGGG AATGGGTGAT GAAAAGGAAG TCACCCAAAT GCTGACCCTA

AATGTCTCCC ATTCCAGTCC CTGAATCACT GGGAGGGCCT TCGGTCTTCA TCTTTCCCCC

GTTTCCCAAG GACATCCTCA GGATTACCCG AACACCCGAG GTCACCTGTG TGGTGTTAGA

TCTGGGCCGT GAGGACCCTG AGGTGCAGAT CAGCTGGTTC GTGGATGGTA AGGAGGTGCA

CACAGCCAAG ACGCAGCCTC GTGAGCAGCA GTTCAACAGC ACCTACCGTG TGGTCAGCGT

CCTCCCCATT GAGCACCAGG ACTGGCTCAC CGGGAAGGAG TTCAAGTGCA GAGTCAACCA

CATAGGCCTC CCGTCCCCCA TCGAGAGGAC CATCTCCAAA GCCAGAGGTG GGCAGCAGGG

CAGAGGGGCT GCAGGGAAGG AGATCTCCCC TGTAGGTCCA GTCCTCCACC CTGATAGTGA

FIG. 17A

```
CCATCTGTGC TGACCCTTTA CCCCACAGGG CAAGCCCATC AGCCCGGTGT GTATGTCCTG

CCACCATCCC CAAAGGAGTT GTCATCCAGT GACACGGTCA CCCTGACCTG CCTGATCAAA

GACTTCTTCC CACCTGAGAT TGATGTGGAG TGGCAGAGCA ATGGACAGCC AGAGCCTGAG

AGCAAGTACC ACACGACTGC ACCCCAGCTG GACGAGGACG GGTCCTACTT CCTGTACAGC

AAGCTCTCTG TGGACAAGAG CCGCTGGGAG CAGGGAGACC CCTTCACATG TGCGGTGATG

CATGAAGCTC TACAGAACCA CTACACAGAT CTATCCCTCT CCCATTCTCC GGGTAAATGA

GCAACACGCC CGGCACCCAG CAAGCCCCCC ACCCTTGGCT CTCAGGATCC
```

DE94 γ  STTAPSVFPLDPSCGSTSGSTVAL ACLVS GYFPEPVTVSWNSGSLTSGVHTFPSDLQSSG
DB31 γ  SSTAPSVFPLAPSCGSTSGSTVTL ACLVS GYFPEPVTVSWNSGSLTSGVHTFPSVLKSSG

Hinge              CH2

DE94 γ  LYSLSSMVTVPSSRWSSETFTCNVAHPASKTKVDKPVPKRENGRVPRPPDCPKCPAPEML
DB31 γ  LYSLSSMVTVPSSRLPSETFTCNVVHPATNTKVDKPGVPKESTCKCIS——PCPVPESL

DE94 γ  GGPSVFIFPPKPKDTLLIARTPEVTCVVVDLGPEDPEVQISWFVDGKQMQTAKTQPREEQ
DB31 γ  GGPSVFIFPPFPKDILRITRTPEVTCVVLDLGREDPEVQISWFVDGKEVHTAKTQPREQQ

CH3

DE94 γ  FNGTYRVVSVLPIGHQDWLKGKQFTCKVNNKALPSPIERTISKARGQAHQPSVYVLPPSR
DB31 γ  FNSTYRVVSVLPIEHQDWLTGKEFKCRVNHIGLPSPIERTISKARGQAHQPGVYVLPPSP
        ↑ GLYCOSYLATION SITE

DE94 γ  EELSKN-TVSLT CL IKDFFPP D IDVEWQSNGQQEPESKYRTTPPQLDEDGSYFLYSKLSV
DB31 γ  KELSSSDTVTLT CL IKDFFPP E IDVEWQSNGQPEPESKYHTTAPQLDEDGSYFLYSKLSV

DE94 γ  DKSRWQRGDTFICAVMHEALHNHYTQKSLSHSPGK
DB31 γ  DKSRWEQGDPFTCAVMHEALQNHYTDLSLSHSPGK

FIG. 18

GGTGGCTCTAGTCATGCATTCCCCTGCTGATTTGCATGTTACCAGAGCACAGCCCACATC

TAAGATTTCTTCAGCTGGTGTTTAGGACAATGGCAGAAAGTCACTCTCAGTGAGGATACA

CCATCAGCATGAGGGTCCTTGCTGAGCTCCTGGGGCTGCTGCTGTTCTGCTTTTTAGGCA
   MetArgValLeuAlaGluLeuLeuGlyLeuLeuLeuPheCysPheLeu
   LEADER

GTGAACAGAGTGAAACGTATGTAATGCTGTCTGATTTGTGATGTATCTACAATTGTTCAC

ATGGTATTGTGTATGTTTCCCACCTCAGGTGTGAGATGTGACATCCAGATGAACCAGTCT
           GlyValArgCysAspIleGlnMetAsnGlnSer
           FR1

CCATCCAGTCTGTCTGCATCCCTTGGAGACACAATTACCATCACTTGCCATGCCAGTCAG
ProSerSerLeuSerAlaSerLeuGlyAspThrIleThrIleThrCysHisAlaserGln
                         CDR1

AACATTAATGTTTGGTTAAGCTGGTACCAGCAGAAACCAGGAAATATTCCTAAACTATTG
AsnIleAsnValTrpLeuSerTrpTyrGlnGlnLysProGlyAsnIleProLysLeuLeu
          FR2

ATCTATAAGGCTTCCAAATTGCACACAGGCGTCCCATCAAGGTTTAGTGGCAGTGGATCT
IleTyrLysAlaSerLysLeuHisThrGlyValProSerArgPheSerGlySerGlySer
  CDR2           FR3

GGAACAGGTTTCACATTAACCATCAGCAGCCTGCAGCCTGAAGACATTGCCACTTACTAC
GlyThrGlyPheThrLeuThrIleSerSerLeuGlnProGluAspIleAlaThrTyrTyr

TGTCAACACGGTCAAAGTTATCCGTACAGCTTCGGAGGGGGGACCAAGCTGGAAATAAAA
CysGlnHisGlyGlnSerTyrProTyrSerPheGlyGlyGlyThrLysLeuGluIleLys
  CDR3        Jk2

CGTAAGTAGTCTTCTCAA

FIG. 20

DOG-MOUSE HETEROHYBRIDOMA AND GENE FRAGMENT CODING FOR CONSTANT REGION OF CANINE IMMUNOGLOBULINS

This application is a continuation of application Ser. No. 08/046,903 filed on Apr. 15, 1993 now abandoned which is a continuation application of application of Ser. No. 07/571,215 filed on Aug. 23, 1990 now abandoned.

FIELD OF THE INVENTION

The present invention relates to a novel canine monoclonal antibody which is expected to be useful for diagnosis, treatment and prevention of canine diseases, especially canine infectious diseases. More particularly, the present invention relates to a novel dog-mouse heterohybridoma capable of producing a canine immunoglobulin, a gene fragment coding for a constant region of canine immunoglobulin and a canine chimeric antibody produced by utilizing said gene fragment.

TECHNICAL BACKGROUND OF THE INVENTION

From ancient times, dogs have been favorably treated as pets by humans. In modern Europe and America, they are called "Companion species" and are now becoming a members of human society. On the other hand, dogs have hitherto been used as an experimental animal in various fields including medicine, pharmacy, animal husbandry, veterinary, psychology etc. They are also used as a SPF dog in recent years in tests for the determination of the effect and safety of drugs, and hence, the usefulness thereof for humans is becoming greater and greater. In any case, it is earnestly desired to establish a method for more certain diagnosis, treatment and prevention of canine diseases, especially canine infectious diseases in order to maintain healthy conditions thereof.

There are many canine viral diseases, and among them, those caused by canine distemper virus, canine parvovirus, infectious canine hepatitis, etc. are acute diseases having a very high mortality rate. Although vaccines for the prevention of these diseases have been developed, only symptomatic therapy such as antibiotics and sulfonamides which prevents secondary bacterial infections has been available for treating those dogs infected and attacked with these diseases, and hence, the conventional methods for treating these diseases are still insufficient.

Hitherto, a hyperimmune serum and an immunoglobulin derived from serum have been utilized for treatment of these diseases and confirmed to be effective. However, with the popularity of the idea for the kind treatment of animals, canine serum materials have become hard to obtain, and hence, this treatment can not be used nowadays. Therefore, development of a monoclonal antibody capable of neutralizing the infected viruses in place of the conventional hyperimmune serum will greatly contribute to the treatment of these viral diseases.

As mentioned above, a monoclonal antibody having a neutralizing activity against viruses can be used as an alternative to the hyperimmune serum. Hitherto, basic techniques of preparing monoclonal antibodies have been established mainly for a mouse monoclonal antibody.

Monoclonal antibodies produced by cells such as hybridomas can advantageously be obtained in a large amount and semipermanently and resolve the problem of material insufficiency. However, the monoclonal antibody in this case should be a canine monoclonal antibody instead of the conventional mouse monoclonal antibody in order to eliminate side effects such as anaphylatic shock, serum disease, etc. caused by the use in dogs of the mouse monoclonal antibody which acts as a heteroprotein to dogs.

Methods for preparing such canine monoclonal antibody as a drug for treating the canine viral diseases include:

(1) a method using a dog-dog hybridoma;

(2) a method using a canine lymphocyte transformed with some viral or chemical agent;

(3) a method using a dog-mouse heterohybridoma;

(4) a method using a dog-(dog-mouse) hybridoma derived from a dog-mouse heterohybridoma; and (5) a method by gene recombination techniques of a mouse (V)-dog (C) chimeric monoclonal antibody wherein a variable (V) region which binds to an antigen is derived from a mouse monoclonal antibody having neutralizing activity against viruses and a constant (C) region which is responsible for antigenicity, immunogenicity and physiological activity is derived from a canine monoclonal antibody.

However, none of the above methods have hitherto been reported to be effectively used.

In the method (1), a fusion efficiency is quite low and no appropriate myeloma strain is available. In case of the method (2), there are no appropriate virus corresponding to EB virus in the case of humans and no appropriate chemical agents. The methods (3) and (4) will have much difficulty (for example, a stability problem etc.) in obtaining the desired canine monoclonal antibody with high efficiency in view of the case of preparation of a human monoclonal antibody. Therefore, it is expected that the method (5) using the chimeric monoclonal antibody is the most realizable method among these five methods.

The chimeric monoclonal antibody is prepared by incorporating a plasmid vector containing a mouse (V)-dog (C) chimeric antibody gene into an animal host cell (e. g. mouse myeloma cell), expressing said gene in the host cell and collecting the monoclonal antibody from a supernatant of the culture, wherein said mouse (V)-dog (C) chimeric antibody gene is such that a V (variable) gene is cloned from a mouse-mouse hybridoma capable of producing a mouse monoclonal antibody as a source of a gene coding for a V region, a C (constant) gene is cloned from a canine cell such as a canine antibody-producing cell capable of producing a canine monoclonal antibody as a source of a gene coding for a C region and said V gene and said C gene are linked to each other. Several reports are found as to human chimeric antibodies (Japanese Patent First Publication Nos. 155132/1985 and 47500/1986).

As mentioned above, a gene coding for an amino acid sequence in a variable (V) region of an antibody molecule capable of binding to a desired antigen and a gene coding for an amino acid sequence in a constant (C) region of a canine immunoglobulin are require for preparing the canine chimeric antibody. The gene coding for the variable (V) region of the chimeric antibody is derived from a cell capable of producing a mouse monoclonal antibody having a neutralizing activity against the above mentioned various canine viruses and said cell can be prepared rather easily by the conventional mouse-mouse hybridoma producing procedures. However, the gene coding for the constant (C) region of the chimeric antibody, i. e. the gene coding for the constant (C) region of the canine immunoglobulin is still unknown in its structure and has never been cloned. Therefore, in order to prepare the canine chimeric antibody, it is inevitably required to find the gene coding for the amino acid sequence of the constant (C) region of the canine immunoglobulin.

In addition, although there is much difficulty for obtaining the monoclonal antibody showing a desired specificity in case of the methods (1) to (4), materials (cell strains) effective for preparing the chimeric antibody can effectively be provided in the case of the method (5) since any cell which produces the canine immunoglobulin regardless of its specificity can preferably be employed as materials for providing a gene coding for the C region of the canine immunoglobulin for preparing the chimeric antibody.

SUMMARY OF THE INVENTION

Under the circumstances, the present inventors have succeeded in preparing dog-mouse hybridomas which produce the canine immunoglobulin, by isolating a gene coding for the amino acid sequence in the constant (C) region of the canine immunoglobulin using said hybridoma cells and canine cells, and in preparing a canine chimeric antibody using the gene fragment coding for the constant (C) region of the canine immunoglobulin.

An object of the invention is to provide a hitherto unreported dog-mouse heterohybridoma capable of producing the canine immunoglobulin and a hitherto genetically unanalyzed DNA fragment coding for an amino acid sequence in the constant (C) region of the canine immunoglobulin. Another object of the invention is to provide a process for preparing the canine chimeric antibody using said DNA fragment coding for the amino acid sequence in the constant (C) region of the canine immunoglobulin, said chimeric antibody being useful as agents for diagnosis, treatment and prevention of canine diseases, especially infectious canine disease, without showing side effects. These and other objects and advantages of the invention will be apparent to those skilled in the art from the following description.

BRIEF DESCRIPTION OF THE DRAWINGS

FIG. 6 shows a nucleotide sequence coding for the constant region of canine immunoglobulin lambda chain present in the DNA fragment (S6–61) cloned by the present invention;

FIG. 7 shows a whole amino acid sequence of the constant. region of canine immunoglobulin lambda chain coded in the DNA fragment (S6–61) cloned by the present invention;

FIG. 11 shows a nucleotide sequence coding for the constant region of canine immunoglobulin kappa chain present in the DNA fragment DEk5a cloned by the present invention;

FIG. 12 shows a whole amino acid sequence of the constant region of canine immunoglobulin kappa chain code in the DNA fragment DEk5a cloned by the present invention;

FIG. 16 shows a nucleotide sequence coding for the constant region of canine immunoglobulin gamma chain present in a DNA fragment DE94gamma cloned by the present invention;

FIG. 17 shows a nucleotide sequence coding for the constant region of canine immunoglobulin gamma chain present in a DNA fragment DB31gamma cloned by the present invention;

FIG. 18 shows whole amino acid sequences of the constant region of canine immunoglobulin gamma chain coded in a DNA fragment DE94gamma and DB31gamma cloned by the present invention;

FIG. 20 shows a nucleotide and an amino acid sequence of a V region gene JP2gL411 isolated from anti-CPV mouse monoclonal antibody-producing cells.

DETAILED DESCRIPTION OF THE INVENTION

Figure 1A:
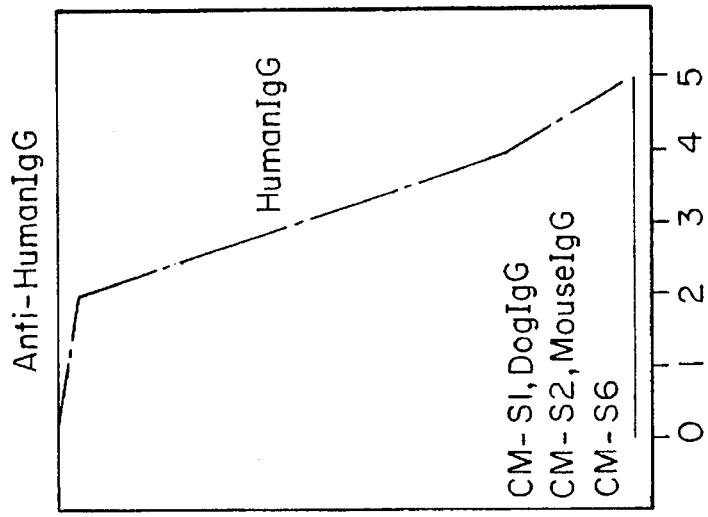
FIG. 1 shows the results of EIA using an anti-canine antibody proving that IgG produced by the dog-mouse hybridomas prepared by the present invention is a canine monoclonal antibody.

There are two approaches for isolating the gene coding for the amino acid sequence in the constant (C) region of the canine immunoglobulin. That is, the first is to construct a library from a chromosomal DNA in canine cells and then to clone the gene coding for the amino acid sequence in C region according to the conventional procedure [for example, see T. Maniatis "Molecular Cloning" Cold Spring Harbor Lab.(1982)], and the second is to construct a library by synthesizing cDNA from a messenger RNA (mRNA) of canine cells and then to clone the C region gene according to the conventional procedure [for example, see "DNA cloning Vol. I" ed. by D. M. Glover, IRL press (1985)].

For the screening procedure, there can be used mainly four processes; i. e. (a) a process which comprises purifying the antibody protein produced by the canine antibody-producing cell, analyzing the amino acid sequence of said protein, and synthesizing a nucleotide sequence corresponding to said amino acid sequence, and then using said nucleotide sequence as a probe for screening (hybridization); (b) a process by cross-hybridization using a probe synthesized by referring to a gene fragment of mouse and human immunoglobulin genes or nucleotide sequences thereof previously reported [for example, Sakano et al., Nature, 286, p676 (1980); E. E. Max et al., J. Biol. Chem., 256, p5116 (1981); J. W. Ellison et al., Nuc. Acids. Res., 10, p4071 (1982); and P. A. Heiter et al., Cell, 22, p197 (1980)]; (c) a process which comprises synthesizing a primer based on a nucleotide sequence on the analogy of an amino acid sequence of a canine antibody protein or a nucleotide sequence on the analogy of the mouse and human immunoglobulin genes previously reported and then screening based on the primer using the PCR procedure [R. Orlandi et al., Proc. Natl. Acad. Sci. USA, 86, p3833 (1989)] and (d) a process which comprises expressing the canine antibody gene incorporated into an expression vector (e.g. Lambda gtll) in *E. coli* or in an animal cell and screening the expression product by using an antiserum (or a monoclonal antibody) directed to the canine antibody protein.

In any case, the screening process using the canine antibody protein-producing cells is preferable in view of the cloning efficiency and is essential in the case of the above second process for isolating the gene using the cDNA synthesized from messenger RNA. Although it is possible to use polyclonal cells such as spleen cells or lymphonodes cells as the antibody-producing cells, monoclonal cells are preferable in view of the easiness of genetic analysis.

There are several methods for establishing the monoclonal antibody-producing cells as cited above (1) to (5). However, the methods (1) and (2) are extremely difficult to practice and the method (4) requires the dog-mouse heterohybridomas of the method (3). In conclusion, it is the most important to obtain the dog-mouse heterohybridomas of the method (3).

The dog-mouse heterohybridomas can be prepared by the several methods previously disclosed. According to these methods, the present inventors have established dog-mouse heterohybridomas CM-S1, -S2, S6 which produce the canine monoclonal antibody. Among these dog-mouse heterohybridomas, CM-S6 are the most preferable cells for preparing the gene of the present invention and has been deposited at the Fermentation Research Institute Agency of Industrial Science and Technology, Japan under Budapest Treaty under the accession number FERM BP-2946.

As mentioned above, the present inventors have cloned several kinds of gene fragments coding for the constant region of immunoglobulin from canine cells. The cloned gene fragments coding for the C region of canine immunoglobulin of the present invention were analyzed by comparing an amino acid sequence deduced from the nucleotide sequence thereof with the corresponding sequences of the C region genes of immunoglobulin from other animal species, and as a result, it has been found that each gene fragment of the present invention contains gene fragments coding for lambda chain, kappa chain and gamma chain, respectively.

Lambda chain of immunoglobulin has already been found in human [P. A. Hieter et al., Nature, 294, p536 (1981); G. F. Hollis et al., Nature 296, p321 (1982)] and in mouse [B. Blomberg et al., Proc. Natl. Acad. Sci. USA, 79, p530 (1982); J. Miller et al., Nature, 295, p428 (1982)] and has also been reported for other animal species such as rabbit [Duvoisin, MR. M. et al., J. Immunol., 136, p4297–4302 (1986)]. However, there has never been reported the canine lambda chain of the present invention, the amino acid sequence thereof and the nucleotide sequence coding therefor.

The cDNA fragment coding for the constant region of canine immunoglobulin lambda chain prepared as mentioned above has been analyzed for its nucleotide sequence. Then, the amino acid sequence of said constant region has been deduced from the nucleotide sequence and compared with the amino acid sequences of the constant region of immunoglobulin lambda chain derived from human, mouse, rabbit, etc. previously reported. As a result, it has been found that the constant region of canine immunoglobulin lambda chain has a specific amino acid sequence at the N-terminal region of the polypeptide of said lambda chain constant region which has the following amino acid sequence (A) at the N-terminal region of the first cysteine counted from the N-terminus of said polypeptide:

-Gly-Ala-xxx-xxx-xxx-xxx-xxx-xxx-Cys-   (A)

wherein xxx mean an optional amino acid residue.

From a comparison among the amino acid sequence of the constant region of canine immunoglobulin lambda chain analyzed in accordance with the present invention, the amino acid sequence of the constant region of feline immunoglobulin lambda chain separately analyzed by the present inventors and various amino acid sequences of the constant region of immunoglobulin lambda chain derived from several animal species, it has been found that the region -Gly-Ala- present at the N-terminus of the above cysteine is a region whose amino acid sequence varies with animal species such dog, mouse, human, etc. In addition, it has been found that this region is quite well preserved among subclasses, for example, as an amino acid sequence of the constant region of human lambda chain, and the above sequence (A) is supposed to be specific for the constant region of canine immunoglobulin lambda chain region cloned by the present invention has the following amino acid sequence (A') which is one example of the preferable specific amino acid sequences present in the constant region of canine immunoglobulin lambda chain.

-Gly-Ala-Asn-Lys-Ala-Thr-Leu-Val-Cys-   (A')

The dog-mouse heterohybridoma of the present invention produces canine immunoglobulin containing a peptide of a lambda chain C region having the above amino acid sequence (A) or (A'). The gene fragment coding for the constant region of canine immunoglobulin lambda chain of the presents invention also contains a DNA fragment coding for the above amino acid sequence (A) or (A'). Such amino acid sequence contained in the above lambda chain is believed to be an important amino acid sequence for determining the C region of canine immunoglobulin lambda chain and is first disclosed by the present invention. In the constant region polypeptide of canine lambda chain, the 11th–9th amino acid sequence at the N-terminal region from the second cystein residue counted from the C-terminus is deemed to be the region whose amino acid sequence varies with species such as dog, cat, human, mouse, etc. as mentioned above, and it is found that the constant region of canine immunoglobulin lambda chain of the present invention has the corresponding specific sequence of -Pro-Asp-Lys-. One preferable example of the gene coding for the constant region canine immunoglobulin lambda chain is a gene fragment coding for the amino acid sequence as shown in FIG. 7 and one example of the nucleotide sequence of said gene is as shown in FIG. 6.

Figure 4:
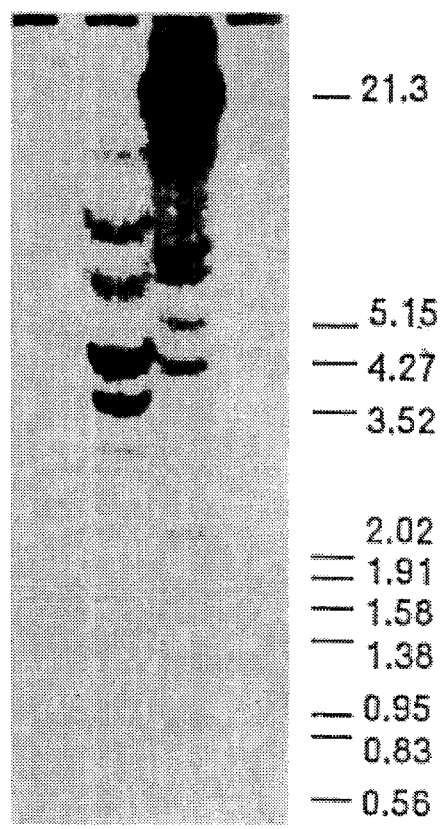
FIG. 4 shows the results of Southern hybridization analysis where a DNA fragment (S6–61) coding for the constant region of canine immunoglobulin lambda chain cloned by the present invention is hybridized with a chromosomal DNA (EcoRI digestion) of canine hepatocytes.

On the analogy of the case of human and mouse [P. A. Hieter et al., Nature, 294, p536 (1981); G. F. Hollis et al., Nature, 296, p321 (1982); B. Blomberg et al., Proc. Natl. Acad. Sci. USA, 79, p530 (1982); J. Miller et al., Nature, 295, p428 (1982)], there is expected an existence of several subclasses in canine lambda chain. In fact, Southern hybridization using the lambda chain gene of the present invention shows an existence of C lambda region genes of several subclasses belonging to the same canine lambda chain gene in addition to the lambda chain of the present invention (FIG. 4). That is, there exists genes of different subclasses having a quite similar sequence to that of the gene fragment coding for the constant region of canine immunoglobulin lambda chain of the present invention. The canine lambda chain gene of the present invention is believed to have sequences which cover also such gene fragments coding for amino acid sequences of different subclasses. Therefore, such gene fragments coding for different subclasses can also be used as the canine lambda chain gene as far as they have a substantially the same sequences as that of the gene of the present invention. Cloning of such C genes of different subclasses can be carried out by using a part of the nucleotide sequence disclosed in the present invention as a probe. Alternatively, a chromosomal gene coding for the canine lambda chain can also be cloned from canine cells using the canine immunoglobulin lambda chain of the present invention as a probe.

Kappa chain of immunoglobulin has also already been found in human and mouse [P. A. Hieter et al., Cell, 22, p197 (1980); H. Sakano et al., Nature 280, p288–294 (1979)] and also reported for other animal species such as rabbit [L. Emorine et al., Proc. Natl. Acad. Sci. USA, 80, p5709–5713 (1983)]. However, there has never been reported for the canine kappa chain of the present invention, an amino acid thereof and a nucleotide sequence coding therefor.

The present inventors have obtained a chromosomal DNA fragment which will code for the constant region of canine immunoglobulin kappa chain by the above-mentioned procedure. The present inventors have also analyzed the nucleotide sequence of the chromosomal DNA fragment and have determined an amino acid sequence of the kappa constant region. As a result of a comparison of the amino acid sequence with those of the constant region of immunoglobulin kappa chain derived from human, mouse, rabbit, etc., it has been found that the gene fragment of the present invention is a gene fragment coding for the constant region of immunoglobulin kappa chain.

The gene fragment coding for the constant region of canine immunoglobulin kappa chain of the present invention is a DNA sequence coding for a peptide comprising 109 amino acids and characterized in that four amino acids at the C-terminus thereof is -Cys-Gln-Arg-Arg-Asp. It is known that the C-terminus of the amino acid sequence of human or mouse kappa chain constant region is Cys (cystein) residue as previously reported. It is very rare that the amino acid sequence of the constant region contains additional four amino acids subsequent to the Cys residue present at the C-terminus like in the gene of the present invention coding for the constant region of canine immunoglobulin kappa chain which is characteristic to the constant region of canine immunoglobulin kappa chain of the present invention. The gene coding for the constant region of canine immunoglobulin kappa chain of the present invention contains the gene fragment as shown by the restriction enzyme map of FIG. 10.

Among the genes coding for the constant region of canine immunoglobulin kappa chain of the present invention, one of the preferable examples is the gene fragment coding for the amino acid sequence as shown in FIG. 12. Such an amino acid sequence coding therefor has hitherto never been reported.

One example of the nucleotide sequence of the gene coding for the C region of canine immunoglobulin kappa chain of the present invention is as shown in FIG. 11. cDNA coding for the C region of immunoglobulin kappa chain can be cloned from a cDNA library of canine antibody-producing cells using the canine immunoglobulin kappa chain of the present invention as a probe.

Gamma chain of immunoglobulin has also already been found in human and mouse [e. g. A. Shimizu et al., Cell, 29, p121 (1982); N. Takahashi et al., Cell, 29, p671 (1982)] and also reported for other animal species such as rabbit [C. L. Martens et al., Proc. Natl. Acad. Sci. USA, 79, p6018 (1982)] and bovine [K. L. Knight et al., J. immunol, 140, p3654 (1988)]. However, there has never been any report concerning the canine immunoglobulin gamma chain.

The present inventors have obtained two chromosomal gene fragments (DE94gamma and DB31gamma )which will code for the constant region of canine immunoglobulin gamma chain by the aforementioned procedure. The cloned gene fragments have genetically been analyzed by comparing an amino acid sequence deduced from the nucleotide sequence of this gene fragment with those of the genes derived from other animal species coding for the C region of immunoglobulin, and as a result, it has been found that the gene fragments obtained by the present invention are a gene fragment coding for the constant region of different subclass of the immunoglobulin gamma chain. The amino acid sequences of each canine gamma chain have been compared with previously reported amino acid sequences of the constant region of immunoglobulin gamma chain derived from human, mouse, rabbit, etc. As a result, it has been found that the amino acid sequence specific for the constant region of canine immunoglobulin gamma chain includes the following amino acid sequence (B) in the vicinity of the second cysteine residue counted from the C-terminus of CH1 domain of the constant region of the gamma chain:

-Ala-Cys-xxx-xxx-Ser-   (B)

wherein xxx represent an optional amino acid.

The present inventors have found that an amino acid sequence of the above region -Ala-Cys-xxx-xxx-Ser- present in the vicinity of the above-mentioned cysteine varies with animal species such as dog, cat, mouse, human, etc. by comparing the amino acid sequence of the constant region of canine immunoglobulin gamma chain analyzed by the present invention with the previously analyzed amino acid sequences of the constant region of immunoglobulin gamma chain derived from various animals. The present inventors have also found that this region is quite well preserved among subclasses(DE94gamma and DB31gamma) of canine gamma chain and also preserved among those of human, rabbit and mouse. The above sequence (B) is believed to be specific for the constant region of canine immunoglobulin gamma chain.

Similar sequences specific for the constant region of canine immunoglobulin gamma chain have also been found in the vicinity of cystein at the N-terminal region of CH3 domain (C):

-Cys-xxx-Ile-xxx-Asp-xxx-Phe-xxx-Pro-   (C)

wherein xxx represents an optional amino acid.

The amino acid sequences of these regions cloned by the present invention have the following sequences (B') and (C') which are each one of the preferable examples of specific amino acid sequences present in the constant region of canine immunoglobulin gamma chain:

-Ala-Cys-Leu-Val-Ser-   (B')

-Cys-Leu-Ile-Lys-Asp-Phe-Phe-Pro-Pro-   (C')

The gene fragments coding for the constant region of canine immunoglobulin gamma chain of the present invention are characterized by that it contains a DNA sequence coding for the above amino acid sequence (B), (C), (B') or (C'). These amino acid sequences contained in the gamma chain, which are quite important for determining the C region of canine immunoglobulin gamma chain, have been found by the present inventors for the first time.

Preferable examples of the constant region of canine immunoglobulin gamma chain containing these amino acid sequences have an amino acid sequence as shown in FIG. 18. Such amino acid sequences and nucleotide sequences coding therefor have never been reported until the present invention.

An example of the nucleotide sequences of the gene coding for the C region of canine immunoglobulin gamma chain of the present invention include the sequences as shown in FIG. 16 and FIG. 17. On the analogy of the human and mouse cases [for example, A. Shimizu et al., Cell, 29, p121 (1982); N. Takahashi et al., Cell, 29, p671 (1982)], the canine gamma chain is also expected to have several subclasses. It is known that there are at least four subclasses of canine gamma chain [J. S. Johnson et al., J. Immunol., 98, p923 (1966)], the genes of the present invention appear to code for two of these four subclasses. In fact, Southern hybridization using the genes of the present invention and a canine chromosomal DNA showed an existence of several genes coding for the C regions of other subclasses of canine gamma chain in addition to the gamma chains of the present invention. That is, there are genes coding for different subclasses having extremely similar sequences to that of the gene of the present invention. In fact, DE94gamma and Db31gamma chain share striking homology with each other, except for those of the hinge regions. It is believed that the canine gamma chain genes of the present invention have sequences which cover also such gene fragments coding for amino acid sequences of different subclasses. Therefore, such gene fragments coding for amino acid sequences of different subclasses can also be used as canine gamma chain gene as far as they have substantially the same sequence as that of the gene of the present invention. Such genes coding for C regions of different subclasses can be cloned by using a part of the nucleotide sequence of the present invention as a probe.

As far as the constant region of immunoglobulin is concerned, it is also reported that a genetic analysis of immunoglobulins derived from human, rabbit, etc. showed an existence of an allotype which differs in one to several amino acids within the same class or subclass. Therefore, the gene coding for the constant region of canine immunoglobulin lambda chain, kappa chain or gamma chain of the present invention is not limited to the gene fragments coding for the above-mentioned amino acid sequences but includes those genes coding for the constant region of different allotypes which have almost the same sequence as the above sequences though containing a partial substitution of an amino acid.

The thus prepared gene coding for the constant region of canine immunoglobulin of the present invention allows for preparation of the canine chimeric antibody using the conventional process for preparing the chimeric antibody [for example, Watanabe et al., Cancer Research, 47, p999–1005 (1987); Japanese Patent First Publication No. 20255/1988]. That is, the chimeric gene can basically be constructed by linking two kinds of gene fragments, i. e. the V region gene and the C region gene, to each other. Since the gene can be classified into mainly two categories depending on a way of isolation, the chimeric antibody can be constructed by using either a combination of V and C region genes isolated from a chromosomal DNA or a combination of V and C region genes isolated from cDNA. The chimeric antibody can be expressed in any expression system such as an animal cell expression system, an *E. coli* expression system, a yeast expression system, etc. using different expression vectors.

In a combination of the V region and the constant region for preparing the chimeric antibody, a preferable combination is the VH region with the constant region derived from canine H chain such as gamma chain, the V kappa region with the constant region of canine kappa chain, and the V lamba region with the constant region of canine lambda chain, but another combination can also be used. There can be used any V region including those derived from mouse, dog, or other animals, and CDR graft V region [M. Verhoeyen, C. Milstein, G. Winter, Science, 239, p1539 (1987)], as far as it is effective for treating canine diseases (e. g. viral canine diseases, etc.). Thus, although it is described as to the mouse-dog chimeric antibody against canine parvovirus to exemplify the canine chimeric antibody of the present invention, the V region is not limited to that used therein.

The gene fragment coding for canine immunoglobulin provided by the present invention discloses the specific amino acid sequence or DNA sequence in the constant region of canine immunoglobulin, and hence, allows for isolating those genes coding for the constant regions belonging to different subclasses or allotypes. By using the gene coding for the constant region of canine immunoglobulin of the present invention, the canine chimeric antibody can firstly be prepared. The canine chimeric antibody prepared according to the present invention can be used as agents for diagnosis, prevention and treatment of canine diseases which have hitherto never been developed.

The present invention is illustrated by the following Examples in more detail but should not be construed to be limited thereto.

EXAMPLE 1

Preparation of Canine Monoclonal Antibody-Producing Cells:

(1) Immunization and Preparation of Canine Lymphocytes:

In order to efficiently obtain activated canine B cells, a complete Freund's adjuvant (CFAa: manufactured by Difco)(5 ml) was injected to dogs subcutaneously and intraperitoneally for several times at an interval of 2 to 3 weeks for nonspecific immunization. Two to three weeks after the final immunization, spleen and lymphonode were taken out and a suspension of canine lymphcytes was obtained by crushing with a pincette and pipetting. One dog gave 1 to $3\times10^9$ cells from spleen and 1 to $3\times10^8$ from lymphonode. These lymphocytes were suspended in a complete medium of RPMI 1640 plus 10% fetal calf serum (manufactured by Flow Laboratories) supplemented with L-glutamine (manufactured by Flow Laboratories) at a concentration of 5 to $10\times10^5$ cells/ml and thereto was added poke-weed mitogen (PWM: manufactured by Gibco)(2.5 µg/ml), followed by culturing the cells in the presence of 5% $CO_2$ at 37° C. for 2 to 5 days for activation.

(2) Preparation of Mouse Myeloma Cells:

The myeloma cells employed in the present invention are those derived from mouse Balb/c as described in Köller et. al., Nature 256, p459 (1975) and Eur. J. Immunol., 6, p292 (1976), especially substrains X63-Ag8-6.5.3 and P3-X63-Ag8-U1, SP2/0Ag12. These cells were cultured and grown in a complete medium of RPMI 1640 plus 10% fetal calf serum supplemented with glutamine. They were collected just before cell fusion, washed twice with RPMI 1640 medium and resuspended in the same medium for use in cell fusion.

(3) Cell Fusion of the Canine Lymphocytes and the Mouse Myeloma Cells:

The above canine lymphocytes and mouse myeloma cells were mixed at a ratio of 10:1 or 5:1 (canine lymphocytes: myeloma cells; canine lymphocytes=$1\times10^8$ cells) and centrifuged at 1,500 rpm for 5 minutes. To the obtained cell pellet was added a 45% polyethylene glycol solution diluted with RPMI 1640 (manufactured by Sigma, pH 7.6, MW 3,650, or manufactured by Celba, pH 7.6, MW 4,000)(1 ml) at room temperature over 1 minute. After the mixture was allowed to stand at 37° C. for 5 to 10 minutes, the cells were resuspended by adding RPMI 1640 (40 ml) to the mixture over 6 minutes to quench the cell fusion. The cells were then centrifuged at 1,000 rpm for 10 minutes, the supernatant was removed by suction, the resulting cell pellet was resuspended in RPMI 1640+10% fetal calf serum+HAT (H: hypoxanthine 13.0 µg/ml, A: aminopterin 0.18 µg/ml, T: thymidine 3.87 µg/ml; all manufactured by Sigma)supplemented with glutamine at a concentration of 2 to $10\times10^5$ lymphocytes/ml. The suspension was poured into each well of a 96-well microtiter plate at 200 µl/well and was cultured in the presence of 5% $CO_2$ at 37° C. After 5 to 7 days, 50% of the medium was exchanged with the same fresh medium and thereafter the medium exchange was repeated for 5 to 6 times after 10 to 28 days from the cell fusion. By this procedure, only hybridoma were grown, and thereafter the cell culture was continued until the screening assay.

(4) Screening Assay and Cloning of Hybridoma:

Screening assay was conducted to detect a clone which produce a canine IgG antibody using enzyme immunoassay (EIA). A 96-well plate was coated with a goat anti-canine IgG antibody (manufactured by Cappel) and treated with bovine serum albumin (manufactured by Sigma) to block non-specific adsorption to each well was added the culture supernatant (50 µl) from each well of the hybridoma culture plate. After incubating the plate at 37° C. for 1 to 2 hours, washing was carried out with PBS-T {0.01% Tween manufactured by Katayama Kagaku K. K., 0.01M phosphate buffer, pH 7.2, 0.15M NaCl} four times, a peroxydase-labelled goat anti-canine IgG antibody (manufactured by Cappel, 10,000 fold dilution)(50 µl) was added to each well and plate was incubated at 37° C. for 1 hour. After washing with PBS-T five times, TMBZ substrate solution (TMBZ: manufactured by Dojin Kagaku K. K., 0.4 mg/ml, hydrogen peroxide: manufactured by Mitsubisi Gasu Kagaku K. K., 0.006%)(50µl) was added to develop color. After 10 to 15 minutes, 0.3N $H_2SO_4$ (manufactured by Katayama Kagaku K. K.)(50 µl) was added to each well to quench the reaction and each color development was quantitated with a spectrophotometer (wavelength: 450 nm). The hybridomas in the thus selected canine IgG-producing well were then monoclonalized (cloned) by a limiting dilution procedure. After growth of the clones in each well of the 96-well plate, the above enzyme immunoassay (EIA) was repeated to detect the canine IgG-producing clone. This cloning procedure was repeated at least 3 times to give the dog-mouse hybridoma clone which stably produce canine IgG. This hybridoma clone was successively subject to an extensive culture and was kept in the frozen state with a cell-freezing medium of RPMI 1640+HAT+10% DMSO supplemented with glutamine in liquid nitrogen.

(5) Characterization of the Established Hybridoma Clone and Canine IgG Monoclonal Antibody Produced Therefrom:

Measurement with an EIA procedure of an amount of the produced canine antibody confirmed that the established dog-mouse hybridomas were capable of stably producing the canine IgG monoclonal antibody in an amount of 1.0 to 3.0 µg/ml for a long time of 1 year or more and any abnormality was not observed in their ability of producing the antibody.

Figure 1B:
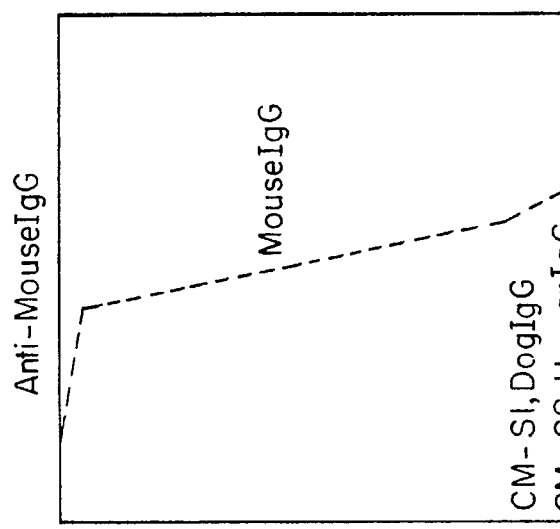
Figure 1C:
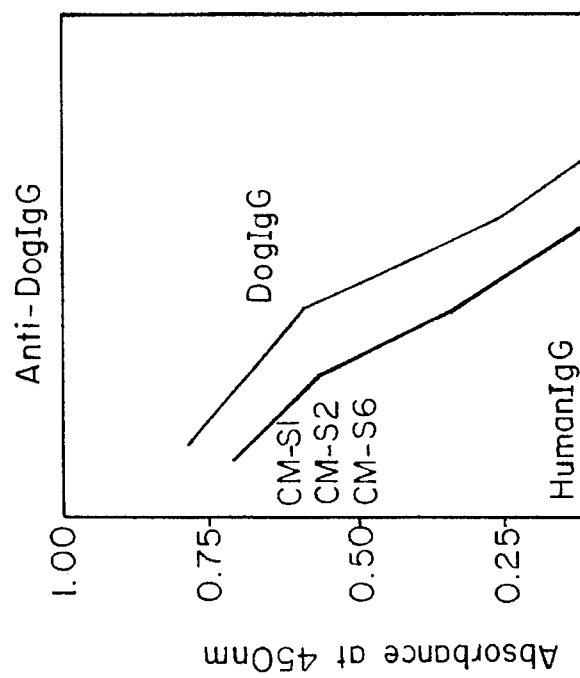
Figure 2:
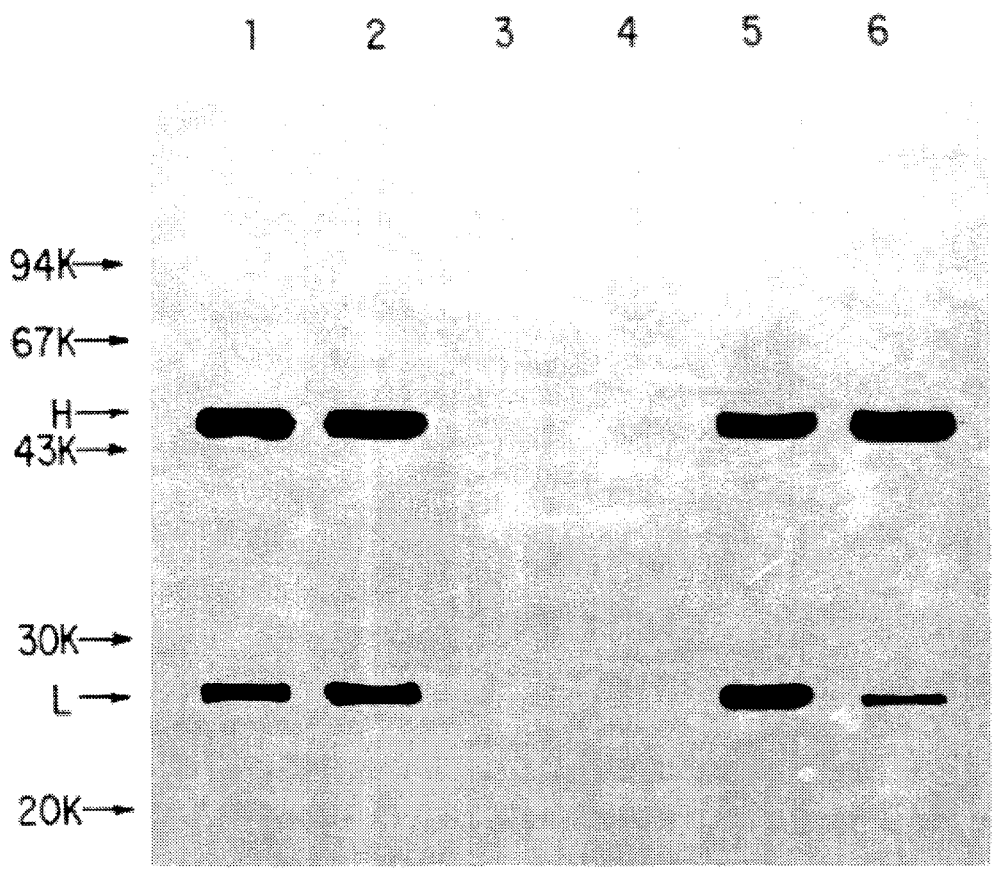
FIG. 2 shows the results of Western blot analysis using an anti-canine antibody proving that IgG produced by the dog-mouse hybridomas prepared by the present invention is a canine monoclonal antibody.

The canine monoclonal antibody produced by the established dog-mouse hybridoma was proven to be canine IgG by an immunoprecipitation method {cf. "Meneki Jikken Sosaho (Immunological Experimentation)" ed. Jap. Soc. Immunol.}. This antibody was found to be canine IgG antibody since it did not form precipitates with goat anti-mouse IgG serum and goat anti-human IgG serum but did form precipitate with goat anti-canine IgG serum. EIA further proved that the monoclonal antibody was canine IgG antibody since it specifically reacts with only the anti-canine IgG antibody but react with neither the anti-human IgG antibody nor the anti-mouse IgG antibody (FIG. 1). Furthermore, Western blotting assay proved that both heavy chain (H chain) fragment and light chain (L chain) fragment of the monoclonal antibody specifically react only with the anti-canine IgG antibody but did not react with the anti-human IgG antibody or anti-mouse IgG antibody and that the H chain fragment and L chain fragment of the monoclonal antibody were identical to those fragment of standard canine IgG antibody in view of molecular weight, showing that the monoclonal antibody is a complete canine IgG monoclonal antibody having both H chain and L chain fragment of the canine IgG antibody (FIG. 2).

In addition, cytoplasmic synthesis of canine IgG antibody was studied by fluorescent antibody dying assay of the hybridoma clone. As a result, each clone was intracytoplasmically dyed specifically only with the anti-canine IgG antibody but was not dyed with the anti-human IgG antibody and the anti-mouse IgG antibody, proving that the hybridoma clones intracytoplasmically synthesized a complete canine IgG monoclonal antibody.

The dog mouse heterohybridoma CM-S6 cells producing such canine monoclonal antibody have been deposited under accession number BP-2946 as mentioned hereinbefore. The CM-S6 cells were used in the following Experiment to isolate the constant region of canine immunoglobulin.

EXAMPLE 2

Cloning of the Gene Coding for the Constant Region of Canine Immunoglobulin Lambda Chain (1) Construction of a cDNA Library:

Total RNA was separate from the heterohybridoma CM-S6 using a guanidium@tricyanate method {J. M. Ghingwin et al., Biochemistry, 18, p5294 (1979)} and further purified into poly A+RNA using an oligo dT column (Pharmacia). cDNA of the CM-S6 cells was synthesized from the purified poly A+RNA using a cDNA synthesis system Plus (Amersham). EcoRI sites of the synthesized cDNA were methylated with EcoRI methylase (manufactured by Takara Shuzo Co. Ltd., the reagents used hereinafter are manufactured by Takara Shuzo Co. Ltd., or Toyobo Co. Ltd., unless otherwise mentioned) and then EcoRI linker was added to the cDNA with T4DNA ligase. This cDNA was completely digested with the restriction enzyme EcoRI and cDNA having an addition of EcoRI linker was purified with a Bio Gel A50m column (Bio-Rad). The obtained cDNA was ligated to an EcoRI arm of λgt11 vector DNA (Stratagene) with T4DNA ligase and then an in vitro packaging was carried out using kits manufactured by Stratagene to give a cDNA library of the CM-S6 cells.

Figure 3:
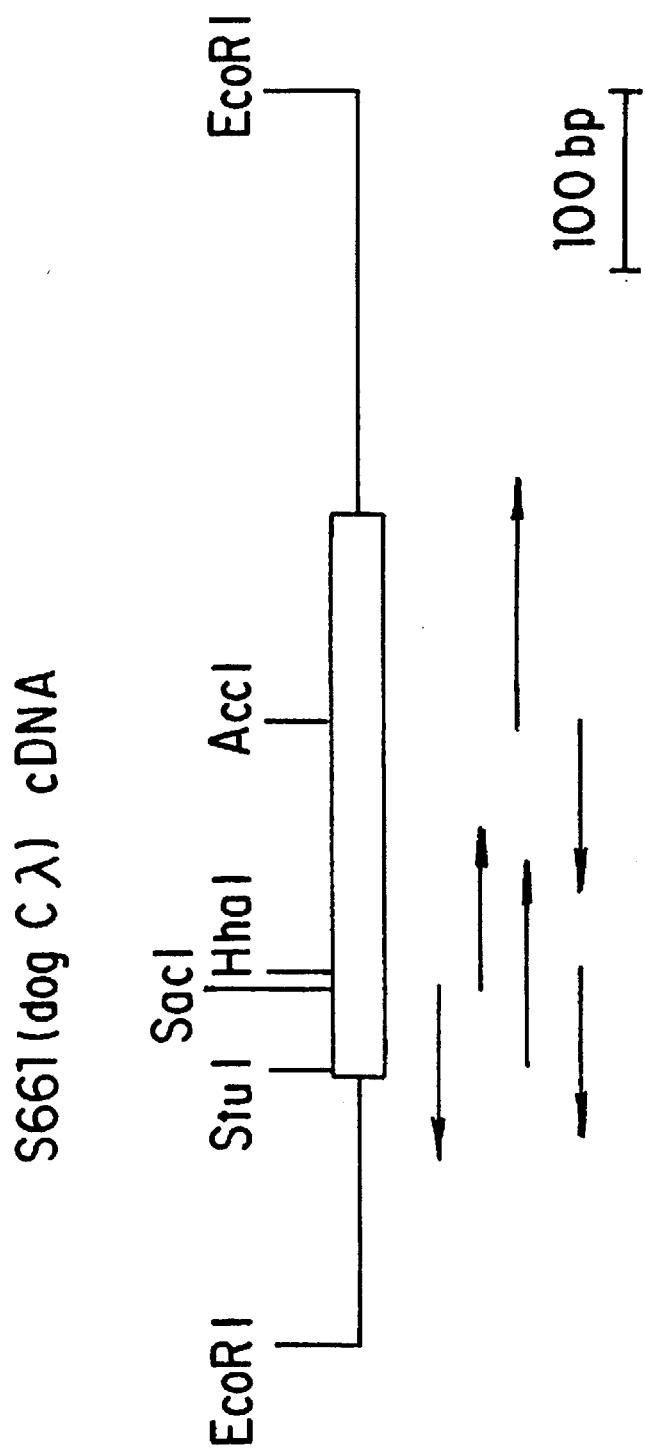
FIG. 3 shows a restriction enzyme map of a DNA fragment (S6–61) coding for the constant region of canine immunoglobulin lambda chain cloned by the present invention and the regions (→) in which a nucleotide sequence was analyzed.

(2) Screening of the Canine Immunoglobulin Gene with Anti-Canine Antibody:

Using the cDNA library of CM-S6 cells constructed as mentioned above, E. coli Y1090 strain cells infected with the phage λgt11 were poured onto an LB plate {laboratory dish of No.2 square manufactured by Eiken Kizai charged with 1.5% Bacto-agar manufactured by Gifco, 1% Bacto-tryptone manufactured by Gifco 0.5% Bacto-yeast extract manufactured by Gifco, 0.25% NaCl manufactured by Wako Pure Chemical Industries, pH 7.5} so that 50,000 plaques per plate of the λgt11 phage were formed and cultured at 42° C. for 3 hours. After covering a nitrocellulose filter (NC filter: Code BA85 manufactured by S&S) soaked with 10 mM IPTG (manufactured by Wako Pure Chemical Industries) on the plate, the Culture was continued at 37° C. for additional 4 hours. The NC filter was peeled off the plate, washed with a W buffer {WB: 7 mM Tris buffer, pH 7.2, 150 mM NaCl, 0.005% Tween 20} and immersed in BLOTTO {5% skim milk, 10 μl/100 ml Antiform A} at 4° C. overnight. Then the BLOTTO was exchanged with a BLOTTO containing an anti-canine IgG antibody {manufactured by Cappel; 10 μg/ml; treated with a 1% E. coli lysate (manufactured by Bio-Rad) at 4° C. overnight} and the reaction was conducted at room temperature for 2 hours. After washing the NC filter with WB five times, the NC filter was immersed in an incubation buffer {PBS, pH 7.2, 0.005% Tween 20, 1% BSA} containing a peroxydase-labelled goat IgG antibody {manufactured by Cappel; treated with a 1% E. coli lysate( manufactured by Bio-Rad) at 4° C. overnight and the reaction was conducted at room temperature for 2 hours. After washing the NC filter with WB five times, the NC filter was immersed in a color development solution containing 5% HRP color development reagent (manufactured by Bio-Rad) and 0.5% $H_2O_2$ (manufactured by Wako Pure Chemical Industries) to proceed color development. After selection of the color development on the NC filter, the phage was further cloned. The clone was selected in this way which react with the anti-canine IgG antibody and finally a clone S6–61 was obtained. This clone had a 0.7 kb size and seemed to be a gene coding for the lambda chain in accordance with the nucleotide sequence analysis as described hereinafter. FIG. 3 shows a restriction enzyme map of this clone.

(3) Southern Blotting and Northern Blotting Analysis Using S6–61:

Southern blotting analysis was carried out using S6–61. A chromosomal DNA (10 μg) from canine, feline and mouse hepatocytes was digested with the restriction enzyme EcoRI and the obtained DNA fragments were subjected to electrophoresis using 0.7% agarose gel. After transfer to nylon membrane filter (Gene Screen Plus, NEN Research Product), the southern hybridization was carried out with a {$^{32}$P}-labeled S6–61 probe containing the constant region of canine lambda chain. The southern hybridization was carried out in accordance with a protocol of manual attached to the Gene Screen Plus. The molecular size was calculated based on the marker DNA which was prepared by digesting the λphage DNA with Hind III. As shown FIG. 4, several bands having various sizes from about 2 to about 20 kb were detected. This suggests that the gene coding for the C region of canine lambda chain has more subclass, which can also be estimated on the analogy of the cases of human and mouse {P. A. Hieter et al., Nature, 294, p536 (1981); G. F. Hollis et al., Nature, 296, p321 (1982); B. Blomberg et al., Proc. Natl. Acad. Sci. USA, 79, p53 (1982); J. Miller et al., Nature, 295, p428 (1982)}. Since it is known that the gene coding for the C lambda region is amplified in wild mice {C. L. Scott et al., Nature, 300, p757 (1982)}, the gene coding for the C region of canine lambda chain can also presumably be subjected to amplification.

Figure 5:
FIG. 5 shows the results of Northern hybridization analysis where a DNA fragment (S6–61) coding for the constant region of canine immunoglobulin lambda chain cloned by the present invention is hybridized with poly A+RNA of CM-S6 cells (lane 1) or CM-1 (lane 2)

Northern blotting was then conducted. The RNA for use in the hybridization was prepared by screening a whole RNA from CM-S1 and CM-S6 cells using a guanidium thiocyanate method {J. M. Ghingwin et al., Biochemistry, 18, p5294 (1979)} and purifying the whole RNA into a poly A+RNA with oligo dT column (Pharmacia). The RNA (2 μg) was electrophoresed using 0.75% agarose gel containing 3% formaldehyde. After transfer to nylon membrane filter (Gene Screen Plus), a northern hybridization was carried out in accordance with a protocol of a manual attached to the Gene Screen Plus. As a result, this probe detected a band at about 1.3 kb in both mRNA (FIG. 5). This size is almost the same as that of the gene coding for immunoglobulin lambda chain known in mouse and human.

From the above two results, the S6–61 gene was presumed to be an active gene coding for a functional canine C lambda region.

(4) Nucleotide Sequence and Amino Acid Sequence of S6–61:

In order to determine a nucleotide sequence of S6–61, small DNA fragments EcoRI-SacI, SacI-AccII, AccII-EcoRI, StuI-EcoRI and EcoRI-HhaI were prepared (FIG. 3). These small fragments were blunt-ended with T4-DNA polymerize and inserted into a SmaI site of a M13mp19 vector using a Takara ligation kit. Competent cells of JM109 were prepared in accordance with a Toyobo Instruct Manual and transformed with M13mp19 DNA wherein the C lambda gene was inserted DNA. A determined using a Takara M13 Sequencing kit and Fuji Genser Gel System. The direction of determination of the nucleotide sequence is shown in FIG. 3. As a result of the determination of the nucleotide sequence, it was confirmed that the canine lambda chain gene consisted of V, J and C region (FIG. 6). FIG. 7 shows the results thereof. The amino acid sequence suggested that the gene is in an open reading frame and is not a pseudogene.

The homology of the nucleotide sequence of S6–61 was searched on data base, LASL and EMBL, using a software for genetic analysis (Genetyx Ver.6 manufactured by Software Kaihatsu, K. K.). As a result, the highest homology was shown with that of human immunoglobulin lambda chain gene but no homology was shown with that the immunoglobulin lambda@chain gene. Homological comparison of the C lambda region of the S6–61 gene with those of mouse and human showed 75.2% homology with mouse and 84.8% homology with human in the nucleic acid level and 73.1% homology with mouse and 84.6% homology with human in the amino acid level.

As is clear from the above results, the S6-61 gene is surely a gene coding for the canine lambda chain which can be used for the preparation of the chimeric antibody.

EXAMPLE 3

Cloning of the Gene Coding for Constant Region of Canine Kappa Chain:

(1) Conditions of Crosshybridization:

The L chain of canine immunoglobulin is known to mainly consist of lambda chain {L. Hood et al., Cold Spring Harbor Symp. Quant. Biol. 32, p133 (1967)}, and hence, it is foreseeable that only quite a few lymphocytes express kappa chain. In fact, the dog-mouse heterohybridoma as described above were lambda chain producing cells. Therefore, the present inventors have considered that it would be very difficult to obtain the desired gene from mRNAs of polyclonal antibody-producing cells by a cDNA cloning procedure, and hence, have tried to isolate the desired gene fragment for the constant region of canine immunoglobulin kappa chain from a chromosomal DNA of canine hepatocytes under crosshybridization conditions using the constant region of human kappa chain (human C kappa) as a probe.

For cloning of the canine kappa chain gene by a crosshybridization procedure, the conditions of crosshybridization with human kappa chain were studied. The gene coding for the human C kappa region used for the crosshybridization was a gene cloned from a human culture cell ARH77 strain {ATCC CRT 1621} which is available from professor Takesi Watanabe, Department of Molecular Immunology, Medical Institute of Bioregulation, Kyushyu University {cf. Kudo et al., Gene, 33, p181, (1985); Nishimura et al., Cancer Res., 47, p999 (1987)}. From this human C kappa gene, an EcoRI-EcoRI fragment containing C kappa exon was obtained and used as a probe.

Figure 8:
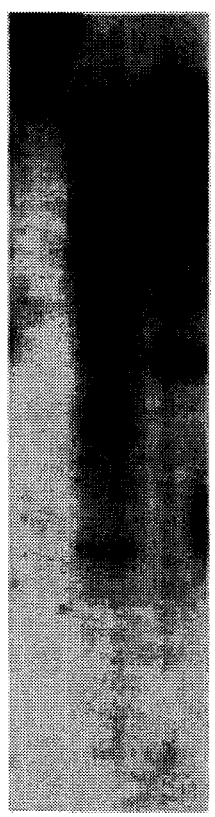
FIG. 8 shows the results of Southern hybridization analysis where a chromosomal DNA of canine hepatocytes is hybridized with [$^{32}$P]-labeled probe containing human C kappa chain region.

Chromosomal DNAs were isolated from canine hepatocytes according to N. Blin and D. W. Stafford [Nuc. Acids. Res., 3, p2303 (1976)] and each 10 µg of the chromosomal DNA was digested with the restriction enzyme EcoRI. DNA fragments obtained by the restriction enzyme digestion were subjected to electrophoresis using 0.7% agarose gel. The developed DNAs were transferred to a nitrocellulose membrane filter (BA85 manufactured by S&S) and then southern hybridization was carried out with a [$^{32}$P]-labeled DNA probe containing human C kappa region gene. The southern hybridization was carried out in a solution of 6×SSC [0.09M $Na_3C_6H_5O_7E2H_2O$, 0.9M NaCl], 10 mM EDTA] manufactured by Dojin Kagaku] and 0.5% SDS [manufactured by Bio-Rad] at 65° C. overnight. The final washing of the filter was conducted with a solution of 0.1×SSC and 0.1% SDS at 45° C. for 15 minutes. Autoradiography of this filter showed a band at about 5 kb as shown in FIG. 8. The molecular size was calculated from a marker DNA prepared by digesting λphage DNA with HindIII. This DNA fragment of 5 kb appears to contain the gene coding for canine kappa chain and is used for cloning.

Figure 10:
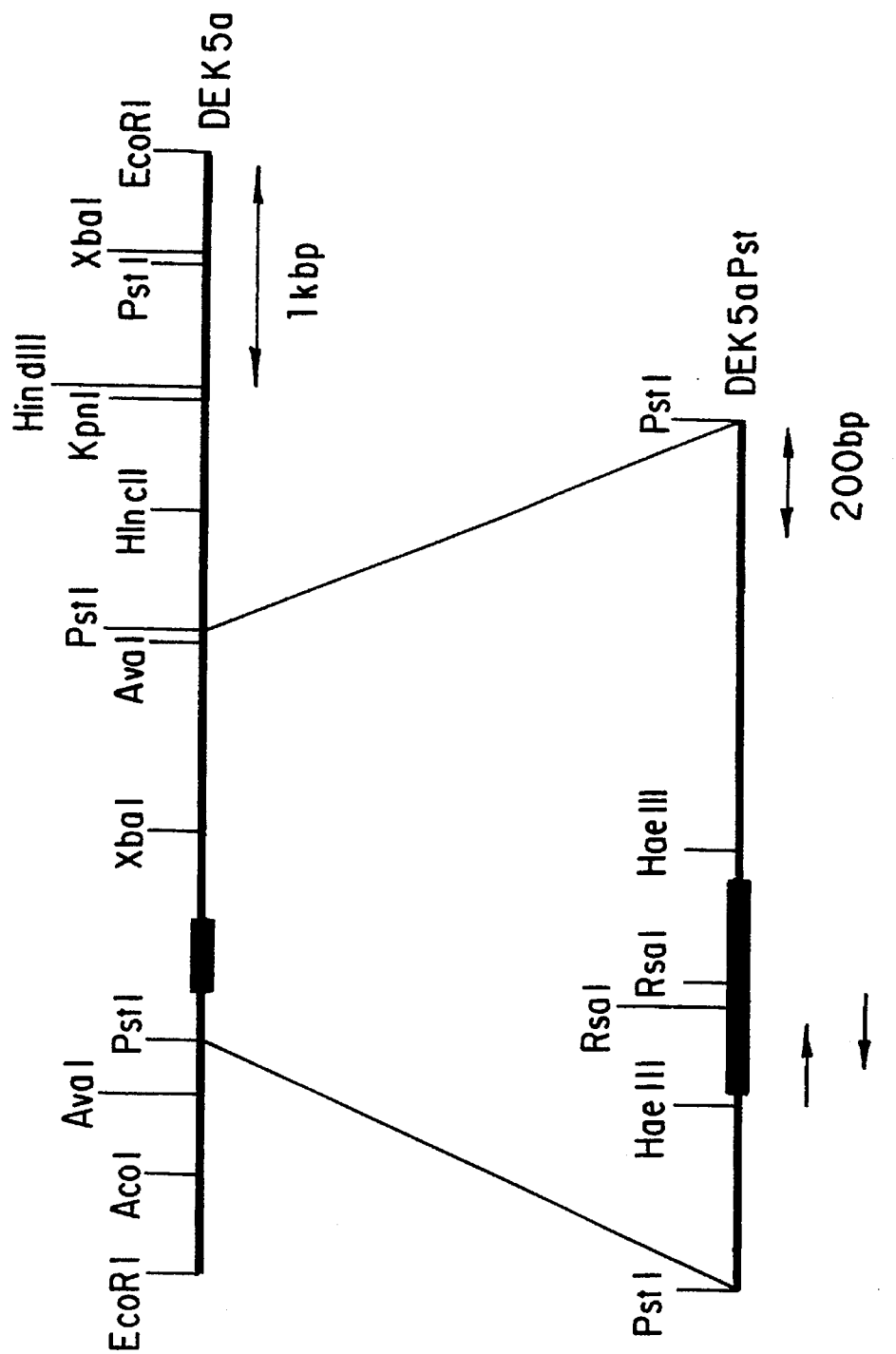
FIG. 10 shows a restriction enzyme map of a DNA fragment (DEk5a) coding for the constant region of canine immunoglobulin kappa chain cloned by the present invention and the regions (→) in which a nucleotide sequence was analyzed.

(2) Isolation of the Gene Coding for Canine Kappa Chain:

A chromosomal DNA (100 µg) from canine hepatocytes was completely digested with EcoRI and DNA fragments of 5 kb were prepared by a sucrose density gradient centrifugation [sucrose 10 to 40% (wt/vol), 26,000 rpm, 18 hours, 15° C.]. The obtained DNA fragments were then ligated to an EcoRI arm of λgt11 vector DNA (manufactured by Stratagene) with T4 DNA ligase and an in vitro packaging was carried out using a kit available from Stratagene to give a kappa chain gene library of canine hepatocytes. Plaque hybridization [W. D. Benton, R. W. Davis, Science, 196, p180 (1977)] was conducted using a human C kappa probe under the same conditions as those of the above crosshybridization and a clone DEk5a containing a canine C kappa chain exon was selected from the library. FIG. 10 shows a restriction enzyme map of this clone.

(3) Southern Blotting and Northern Blotting Analysis Using DEk5a:

A chromosomal DNA (10 µg) from canine hepatocytes was digested with the restriction enzyme EcoRI and the Southern blotting analysis was conducted using the clone DEk5a in the same manner as described in Example 2 (3). A pattern of the detected bands was compared with that from crosshybridization using a human C kappa chain probe previously conducted, and as a result, a band was observed at the same position (about 5 kb). This result presumably showed that the canine C kappa region gene consists of a single gene without any other subtypes. This is also suggested by the cases of human and mouse [P. A. Hieter er al., Cell, 22, p197 (1989); E. E. Max et al., Proc. Natl. Acad. Sci. USA, 76, p3450 (1979)].

Figure 9:
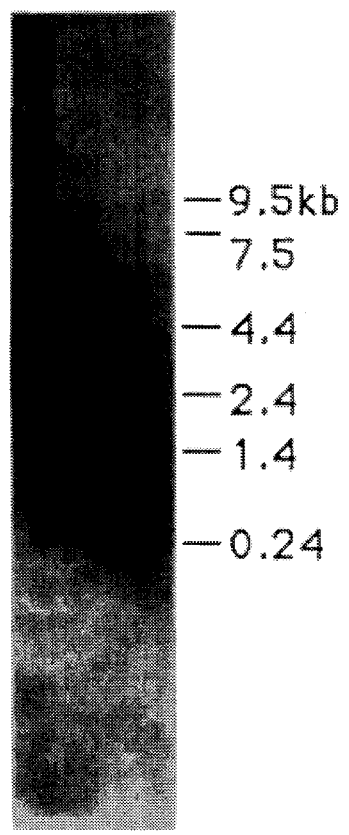
FIG. 9 shows the results of Northern hybridization analysis where poly A+RNA extracted from canine spleen cells is hybridized with a [32P]-labeled DEk5a probe.

Northern blotting analysis was then carried out using the DEk5a clone in the same manner as described in Example 2 (3). As a result, the probe detected a band at about 1.3 kb with mRNA from canine spleen cells (FIG. 9). This is almost the same size as known in the mouse and human immunoglobulin kappa chain gene but the signal of the band is weaker than the case of lambda. This shows that only a few lymphocytes express kappa light chain.

These two results presumably showed that the DEk5a is an active gene containing a gene coding for a functional canine C kappa region.

(4) Nucleic Acid and Amino Acid Sequences of the DEk5a:

In order to determine a nucleic acid sequence of the gene coding for the canine C kappa region, a DNA fragment (PstI-PstI fragment) of about 2.0 kb containing the C kappa region was isolated from the clone DEk5a and recloned into a PstI site of pUC18 vector. This plasmid (pDEK5aPst) was prepared in a large amount in accordance with the conventional method [for example, T. Maniatis "Molecular Cloning" Cold Spring Harbor Lab. (1982)] and from the PstI-PstI fragments were prepared small DNA fragments (PstI-PstI, HaeIII-RsaI, RsaI-RsaI, RsaI-HaeIII, HaeIII-PstI). These small DNA fragments were blunt-ended with T4-DNA polymerase and then inserted into a SmaI site of M13mp19 vector using a Takara Ligation Kit. The nucleotide sequence was determined in the same manner as described in Example 2 (4). A direction of determination of the nucleotide sequence is shown in FIG. 10. As a result of the determination of the nucleic acid base sequence, the C kappa gene comprising a single exon was confirmed. FIG. 11 shows the results thereof. An amino acid sequence deduced from the nucleotide sequence showed that the gene is in an open reading frame and is not a pseudogene (FIG. 12).

The homology of the nucleotide sequence of DEK5a was searched on data bases, LASL and EMBL, using software for of genetic analysis (Genetyx manufactured by Software Kaihatsu, K. K.). As a result, a high homology was shown with gene coding for human and mouse immunoglobulins kappa chain but no homology was shown with genes other than the immunoglobulin kappa chain gene. Homological comparison of the C kappa region of the DEk5a gene with the mouse and human C kappa regions showed 70.0% homology with mouse and 70.1% homology with human in the nucleic acid level and 59.0% homology with mouse and 59.6% homology with human in the amino acid level.

As is clear from the above results, the DEk5a gene is surely a gene coding for the canine kappa chain which can be used for the preparation of the dog-mouse chimeric antibody.

EXAMPLE 4

Cloning of the Gene Coding for Constant Region of Canine Gamma Chain:

(1) Conditions of Crosshybridization:

The present inventors then tried to isolate the canine gamma chain gene by cloning using a crosshybridization procedure as in the case of kappa chain gene.

Figure 13:
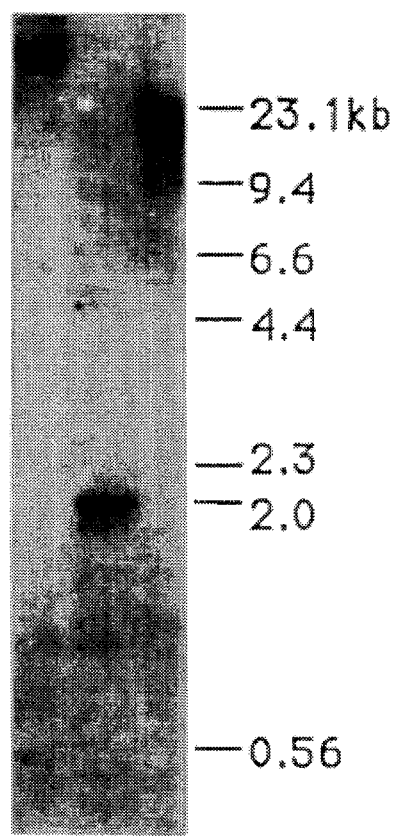
FIG. 13 shows the results of Southern hybridization analysis where a chromosomal DNA of canine hepatocytes is hybridized with a [$^{32}$P]-labeled probe containing the human C gamma 1 chain region.

In the same manner as in Example 3 (1), crosshybridization was carried out using a chromosomal DNA (10 μg) from canine hepatocytes digested with the restriction enzyme BamHI, EcoRI and HindIII and a human C gamma 1 chain as a probe. The gene coding for the human C gamma 1 region used for the crosshybridization was a gene cloned from a human culture cell ARH77 strain [ATCC CRL 1621] which is available from professor Takeshi Watanabe, Kyushu University, Seitai Bogyo Igaku Kenkyuusho [Kudo et al., Gene, 33, p181 (1985); Nishimura et al., Cancer Res., 47, p999 (1987)]. Computerized analysis of homology between mouse, human and rabbit gamma chains showed a extremely high homology especially at the region containing a CH2-CH3 exon. Therefore, a PstI-SphI fragment containing the CH2-CH3 exon was obtained from the human C gamma 1 gene and used as a probe. The result of autoradiography showed four bands at about 2.0, 1.9, 1.3 and 1.05 kb as shown in FIG. 13 (BamHI digested). These bands were targeted for cloning.

Figure 14A:
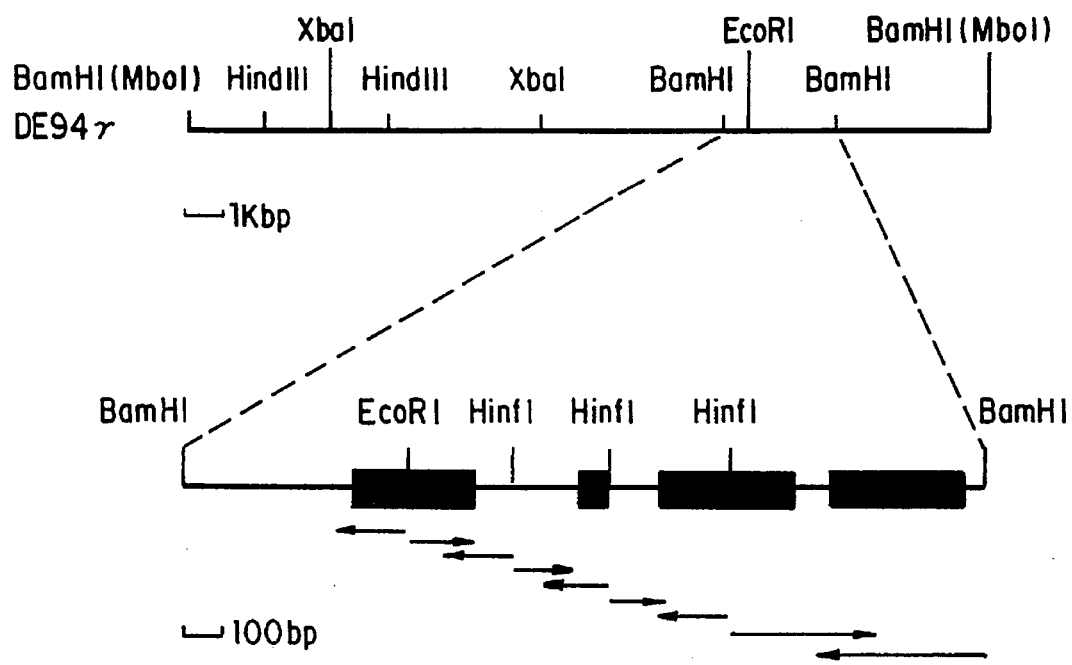
FIG. 14 shows a restriction enzyme map of the chromosomal DNA fragment (DE94gamma,DB31gamma) coding for the constant region of canine immunoglobulin gamma chain cloned by the present invention.
Figure 14B:
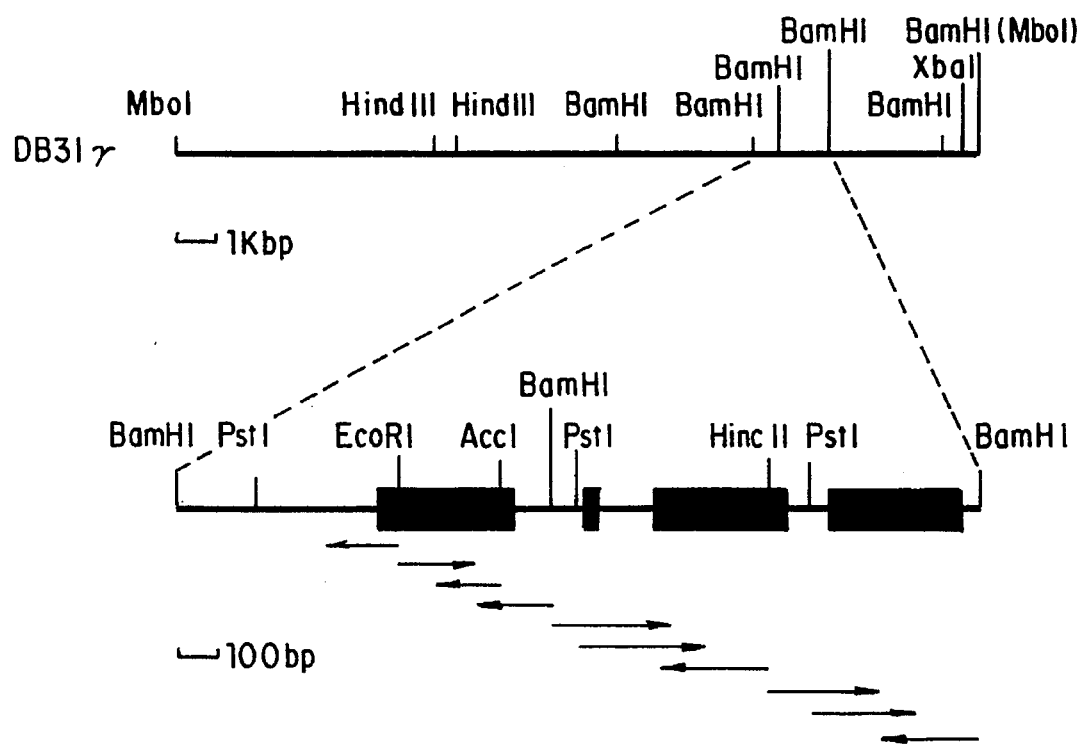

(2) Isolation of the Canine Gamma Chain Gene:

A chromosomal DNA (100 μg) from canine hepatocytes was partially digested with MboI and then DNA fragments corresponding to the above 20 kb and 25 kb were prepared by a sucrose density gradient centrifugation [sucrose 10 to 40% (wt/vol), 26,000 rpm, 18 hours, 15° C.]. Then, the obtained DNA fragments were ligated to a BamHI-digested DNA of λEMBL3 vector DNA (manufactured by Nippon Gene) with T4 DNA ligase and an in vitro packaging was carried out using a kit available from Stratagene. P2392 *E. coli* (Stratagene) was then infected with the resultant recombinant DNA and a gamma chain gene library of canine hepatocytes was obtained. Plaque hybridization [W. D. Benton, R. W. Davis, Science, 196, p180 (1977)] was conducted under the same conditions as those of the above described crosshybridization. Six different clones were obteined after screening 2.0×10⁶ recombinant phages. Southern blot analysis and restriction cleavage mapping have revealed that these clones are classified into two different canine gamma genes. The restriction maps of two canine gamma gene clones, DE94gamma and a DB31gamma, are shown in FIG. 14. BamHI fragment (2.0 kbp) of DE94gamma and BamHI fragment (1.3 kbp) of DB31gamma contain the canine C gamma chain exon. These BamHI fragments were used in the following Examples.

(3) Southern and Northern Blotting Analysis Using DE94gamma and DB31gamma:

A chromosomal DNA (10 μg) from canine hepatocytes was digested with the restriction enzyme BamHI and Southern blotting analysis was conducted using the DE94gamma and DB31gamma clones in the same manner as described in Example 2 (3). Comparison of a pattern of detected bands with that of crosshybridization previously conducted using the human C gamma 1 chain probe showed a band at the same position (the same results as in FIG. 13). This result showed an existence of several C gamma region genes of different subclasses belonging to the same canine gamma chain in addition to the DE94gamma and DB31gamma.

The existence of several subclasses in the canine gamma chain is also suggested on the analogy of the cases of human and mouse [for example, A. Shimizu et al., Cell, 29, p121 (1982); N. Takahashi et al., Cell, 29, p671 (1982)]. It is known that serologically at least four subclasses exist for the canine gamma chain [J. S. Johnson, J. Immunol., 98, p923 (1966)] and the DE94gamma and DB31gamma genes seem to code for two subclasses of the four canine IgG.

Figure 15:
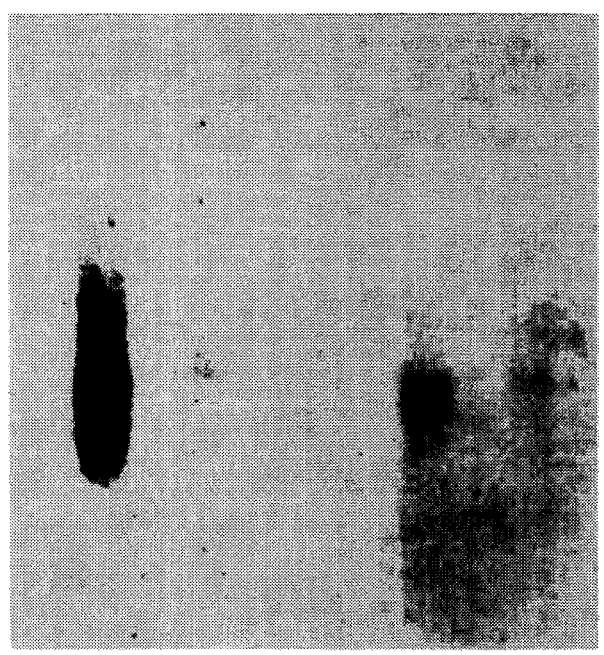
FIG. 15 shows the result of Northern hybridization analysis where poly A+RNA extracted from canine, mouse or feline spleen cells is hybridized with a [$^{32}$P]-labeled DE94gamma or DB31gamma probe.

Then, Northern blotting analysis was carried out using the DE94gamma(a) and DB31gamma(b) clones in the same manner described in Example 2 (3). As a result, the probes specifically detected a band at about 1.8 kb with mRNAs from dog (FIG. 15). This is almost the same size as known in mouse and human immunoglobulin gamma chain genes.

These two results presumably showed that the DE94gamma and DB31gamma clones are active genes containing a gene coding for a functional canine C gamma region.

(4) Nucleic Acid and Amino Acid Sequences of the DE94gamma and DB31gamma:

The nucleotide sequence was determined in the same manner as described in Example 2 (4). A direction of determination of the nucleotide sequence is shown in FIG. 14. As a result of the determination of the nucleic acid sequence, these C gamma genes share striking homology with each other. FIG. 16 and 17 shows the results thereof. An amino acid sequence deduced from the nucleotide sequence showed that the gene is in an open reading frame and is not a pseudogene (FIG. 18).

The homology of the nucleotide sequence of DE94gamma and DB31gamma were searched on data bases, LASL and EMBL, using software for genetic analysis (Genetyx manufactured by Software Kaihatsu, K. K.). As a result, a high homology was shown with gene coding for human and mouse immunoglobulins gamma chain but no homology was shown with genes other than the immunoglobulin gamma chain gene. Homological comparison of the C gamma region of the DE94gamma gene with the mouse and human C gamma 1 regions showed 61.0% homology with mouse, 70.4% homology with human and 80.7% homology with DB31gamma in the amino acid level. On the other hand, DB31gamma gene showed 64.7% homology with mouse and 67.6% homology with human in the amino acid level.

As is clear from the above results, the DE94gamma and DB31gamma genes are surely a gene coding for the canine gamma chain which can be used for the preparation of the dog-mouse chimeric antibody.

EXAMPLE 5

Preparation of Mouse-Dog Chimeric Antibody:

(1)Isolation of Gene Coding for Mouse Immunoglobulin Kappa Chain Variable (V kappa) Region:

In order to show the usefulness of the thus isolated gene coding for the constant region of canine immunoglobulin in the preparation of the chimeric antibody, a chimeric antibody comprising said gene and a gene coding for the variable region of mouse antibody JP-2 having a neutralization activity against canine parvovirus (CPV) was prepared.

Figure 19:
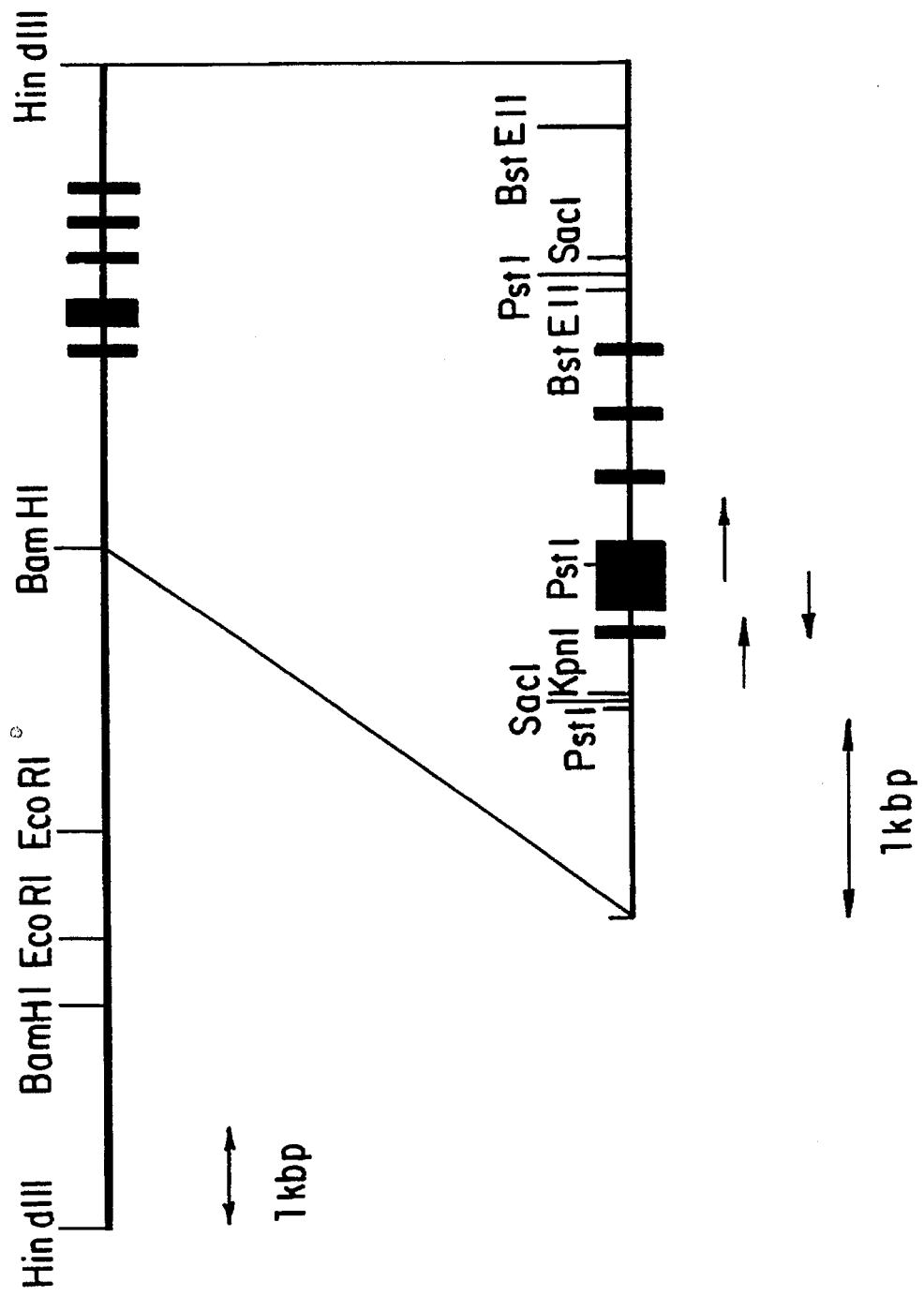
FIG. 19 shows a restriction enzyme map of a clone JP2g L411 containing V kappa region gene isolated from anti-CPV mouse monoclonal antibody-producing cells.

The gene coding for the V kappa region of JP-2 antibody was firstly isolated. A chromosomal DNA (100 μg) isolated from hybridoma JP-2 (gamma 1,kappa) producing an anti-CPV antibody was digested with the restricted enzyme HindIII. These DNA fragments were then ligated to λL47 vector DNA (Amersham) with T4 DNA ligase and a chromosomal DNA library of JP-2 cells was obtained. A clone JP-2gL411 containing the V kappa region gene of the anti-CPV antibody was selected from the library by plaque hybridization procedure [W. D. Benton, R. W. Davis, Science, 196, p180 (1977)] using a mouse J kappa region [E. E. Max et al., J. Biol. Chem., 256, p5116 (1981)]. FIG. 19 shows a restriction enzyme map thereof. From this gene fragment there was prepared a BamHI-HindIII fragment containing a V kappa exon part and the fragment was subjected to Northern hybridization with mRNA of JP-2 and its mother strain P3X63Ag8.U1 to detect a Jp-2 specific band at 1.3 kbp. A nucleotide sequence was determined (FIG. 20) by a DNA sequencing which was made at a direction of an arrow as shown in FIG. 19. An amino acid sequence deduced from the nucleotide sequence was in an open reading frame (FIG. 20), and hence, the gene was shown to code for a functional immunoglobulin V kappa. Based on these results, this V kappa gene was used for preparing a gene coding for an L chain of mouse-dog chimeric antibody.

Figure 21:
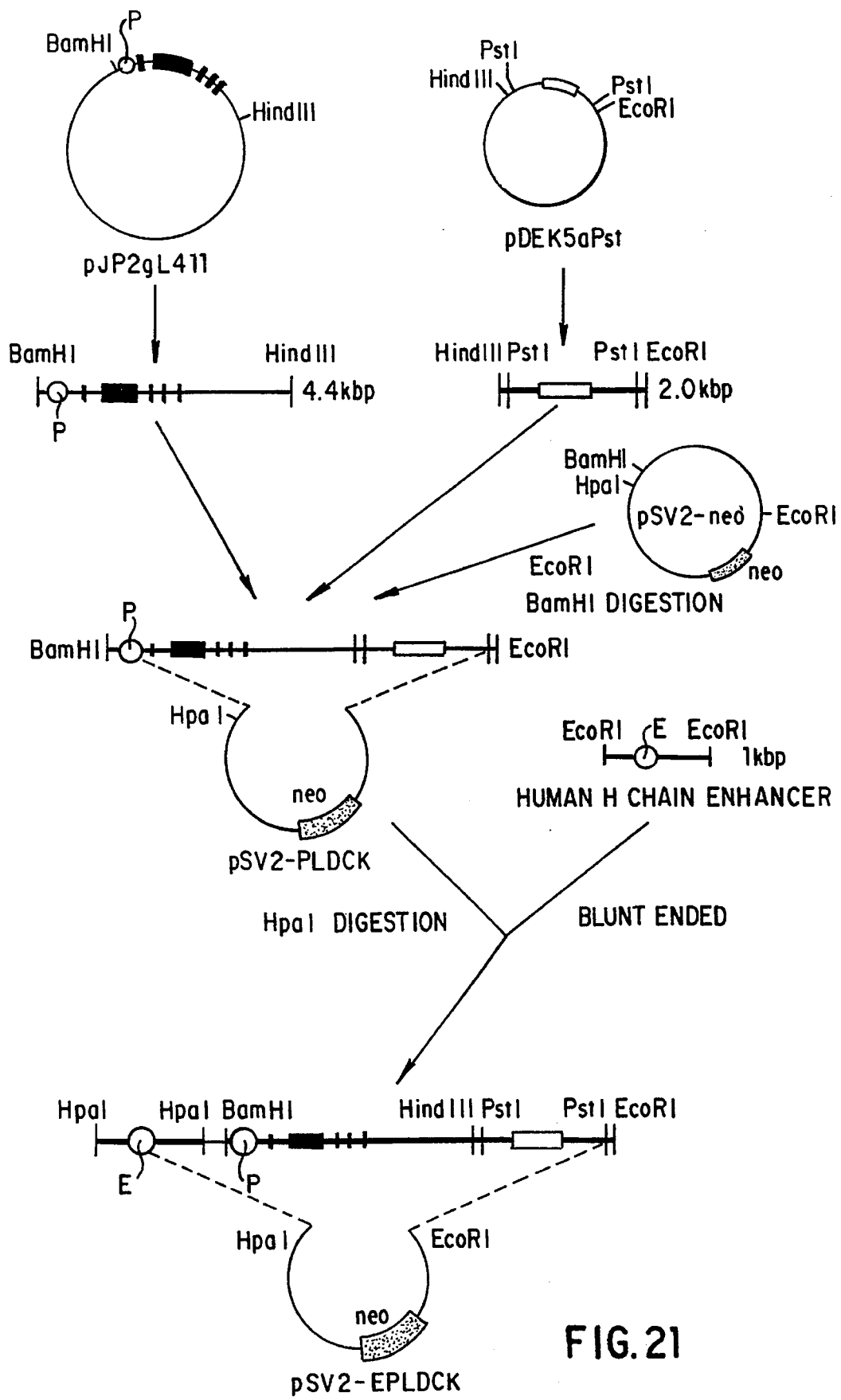
FIG. 21 shows a construction of a gene (pSV2-EPLDCk) expressing an L chain of an anti-CPV mouse-dog chimeric antibody.

(3) Preparation of Gene Coding for L Chain of Mouse Dog Chimeric Antibody (pSV2-EPLDCk):

The plasmid pDEk5aPst prepared in Example 3 (2) was digested with HindIII and EcoRI to prepare a HindIII DNA fragment of 2 kbp containing a gene coding for canine immunoglobulin C kappa. On the other hand, a plasmid pJP2gL411 containing the gene coding for mouse immunoglobulin V kappa chain prepared in Example 5 (1) was digested with BamHI and HindIII to prepare a gene of 4.4 kbp coding for a mouse immunoglobulin V kappa -J kappa region. These genes were ligated to each other together with pSV2-neo vector [P. J. Southern et al., J. mol. Appl. Genet., 1, p327 (1982)] which was digested with EcoRI and BamHI using a Takara Ligation Kit to prepare a plasmid pSV2-PLDCk. The human heavy chain enhancer element was inserted into the HpaI site of this plasmid to prepare a plasmid pSV2-EPLDCk (FIG. 21).

(5) Expression of Mouse-Dog Chimeric Antibody:

The constructed plasmid pSV2-EPLDCk was introduced into a mouse B lymphoma strain Sp2/0-Ag12 (ATCC CRT 1581) in accordance with a method previously reported by Maeda et al. [Japanese Patent First Publication No. 20255/1988] using a DEAE-dextran method. The cells were transformed with the plasmid pSV2-EPLDCk to prepare cells which produce the desired L chain of the mouse-dog chimeric antibody.

As mentioned above, only use of the gene coding for the constant region of canine immunoglobulin as cloned by the present inventors makes it possible to prepare the canine chimeric antibody. The thus prepared canine chimeric antibody can be used as agents for diagnosis, prevention and treatment of canine disease, especially canine infectious disease.

What is claim is:

1. An isolated DNA molecule consisting of a DNA sequence encoding an amino acid sequence of a constant region of a canine immunoglobulin gamma chain, wherein the amino acid sequence of said constant region includes the following amino acid sequences:

-Ala-Cys-Leu-Val-Ser, and

-Cys-Leu-Ile-Lys-Asp-Phe-Phe-Pro-Pro.

2. An isolated recombinant DNA molecule encoding a chimeric immunoglobulin gamma chain, wherein:

the portion of said recombinant DNA molecule encoding the variable region of said chimeric immunoglobulin gamma chain has a nucleotide sequence of a mouse variable region gene;

the portion of said recombinant DNA molecule encoding the constant region of said chimetic immunoglobulin gamma chain has a nucleotide sequence of a canine immunoglobulin gamma constant region gene;

and further wherein the DNA encoding said canine immunoglobulin gamma constant region encodes the amino acid sequences -Ala-Cys-Leu-Val-Ser- and -Cys-Leu-Ile-Lys-Asp-Phe-Phe-Pro-Pro-.

3. An isolated recombinant DNA molecule encoding the constant region of a canine immunoglobulin gamma chain having the amino acid sequence (i):

—Ser—Thr—Thr—Ala—Pro—Ser—Val—Phe—Pro—Leu—Asp

—Pro—Ser—Cys—Gly—Ser—Thr—Ser—Gly—Ser—Thr—Val

—Ala—Leu—Ala—Cys—Leu—Val—Ser—Gly—Tyr—Phe—Pro

—Glu—Pro—Val—Thr—Val—Ser—Trp—Asn—Ser—Gly—Ser

—Leu—Thr—Ser—Gly—Val—His—Thr—Phe—Pro—Ser—Asp

—Leu—Gln—Ser—Ser—Gly—Leu—Tyr—Ser—Leu—Ser—Ser

—Met—Val—Thr—Val—Pro—Ser—Ser—Arg—Trp—Ser—Ser

—Glu—Thr—Phe—Thr—Cys—Asn—Val—Ala—His—Pro—Ala

—Ser—Lys—Thr—Lys—Val—Asp—Lys—Pro—Val—Pro—Lys

—Arg—Glu—Asn—Gly—Arg—Val—Pro—Arg—Pro—Pro—Asp

—Cys—Pro—Lys—Cys—Pro—Ala—Pro—Glu—Met—Leu—Gly

—Gly—Pro—Ser—Val—Phe—Ile—Phe—Pro—Pro—Lys—Pro

—Lys—Asp—Thr—Leu—Leu—Ile—Ala—Arg—Thr—Pro—Glu

—Val—Thr—Cys—Val—Val—Val—Asp—Leu—Gly—Pro—Glu

—Asp—Pro—Glu—Val—Gln—Ile—Ser—Trp—Phe—Val—Asp

—Gly—Lys—Gln—Met—Gln—Thr—Ala—Lys—Thr—Gln—Pro

—Arg—Glu—Glu—Gln—Phe—Asn—Gly—Thr—Tyr—Arg—Val

—Val—Ser—Val—Leu—Pro—Ile—Gly—His—Gln—Asp—Trp

—Leu—Lys—Gly—Lys—Gln—Phe—Thr—Cys—Lys—Val—Asn

—Asn—Lys—Ala—Leu—Pro—Ser—Pro—Ile—Glu—Arg—Thr

—Ile—Ser—Lys—Ala—Arg—Gly—Gln—Ala—His—Gln—Pro

—Ser—Val—Tyr—Val—Leu—Pro—Pro—Ser—Arg—Glu—Glu

—Leu—Ser—Lys—Asn—Thr—Val—Ser—Leu—Thr—Cys—Leu

—Ile—Lys—Asp—Phe—Phe—Pro—Pro—Asp—Ile—Asp—Val

—Glu—Trp—Gln—Ser—Asn—Gly—Gln—Gln—Glu—Pro—Glu

—Ser—Lys—Tyr—Arg—Thr—Thr—Pro—Pro—Gln—Leu—Asp

-continued

—Glu—Asp—Gly—Ser—Tyr—Phe—Leu—Tyr—Ser—Lys—Leu

—Ser—Val—Asp—Lys—Ser—Arg—Trp—Gln—Arg—Gly—Asp

—Thr—Phe—Ile—Cys—Ala—Val—Met—His—Glu—Ala—Leu

—His—Asn—His—Tyr—Thr—Gln—Lys—Ser—Leu—Ser—His

—Ser—Pro—Gly—Lys or (ii):

—Ser—Ser—Thr—Ala—Pro—Ser—Val—Phe—Pro—Leu—Ala

—Pro—Ser—Cys—Gly—Ser—Thr—Ser—Gly—Ser—Thr—Val

—Thr—Leu—Ala—Cys—Leu—Val—Ser—Gly—Tyr—Phe—Pro

—Glu—Pro—Val—Thr—Val—Ser—Trp—Asn—Ser—Gly—Ser

—Leu—Thr—Ser—Gly—Val—His—Thr—Phe—Pro—Ser—Val

—Leu—Lys—Ser—Ser—Gly—Leu—Tyr—Ser—Leu—Ser—Ser

—Met—Val—Thr—Val—Pro—Ser—Ser—Arg—Leu—Pro—Ser

—Glu—Thr—Phe—Thr—Cys—Asn—Val—Val—His—Pro—Ala

—Thr—Asn—Thr—Lys—Val—Asp—Lys—Pro—Gly—Val—Pro

—Lys—Glu—Ser—Thr—Cys—Lys—Cys—Ile—Ser—Pro—Cys

—Pro—Val—Pro—Glu—Ser—Leu—Gly—Gly—Pro—Ser—Val

—Phe—Ile—Phe—Pro—Pro—Phe—Pro—Lys—Asp—Ile—Leu

—Arg—Ile—Thr—Arg—Thr—Pro—Glu—Val—Thr—Cys—Val

—Val—Leu—Asp—Leu—Gly—Arg—Glu—Asp—Pro—Glu—Val

—Gln—Ile—Ser—Trp—Phe—Val—Asp—Gly—Lys—Glu—Val

—His—Thr—Ala—Lys—Thr—Gln—Pro—Arg—Glu—Gln—Gln

—Phe—Asn—Ser—Thr—Tyr—Arg—Val—Val—Ser—Val—Leu

—Pro—Ile—Glu—His—Gln—Asp—Trp—Leu—Thr—Gly—Lys

—Glu—Phe—Lys—Cys—Arg—Val—Asn—His—Ile—Gly—Leu

—Pro—Ser—Pro—Ile—Glu—Arg—Thr—Ile—Ser—Lys—Ala

—Arg—Gly—Gln—Ala—His—Gln—Pro—Gly—Val—Tyr—Val

—Leu—Pro—Pro—Ser—Pro—Lys—Glu—Leu—Ser—Ser—Ser

—Asp—Thr—Val—Thr—Leu—Thr—Cys—Leu—Ile—Lys—Asp

—Phe—Phe—Pro—Pro—Glu—Ile—Asp—Val—Glu—Trp—Gln

—Ser—Asn—Gly—Gln—Pro—Glu—Pro—Glu—Ser—Lys—Tyr

—His—Thr—Thr—Ala—Pro—Gln—Leu—Asp—Glu—Asp—Gly

—Ser—Tyr—Phe—Leu—Tyr—Ser—Lys—Leu—Ser—Val—Asp

—Lys—Ser—Arg—Trp—Glu—Gln—Gly—Asp—Pro—Phe—Thr

—Cys—Ala—Val—Met—His—Glu—Ala—Leu—Gln—Asn—His

—Tyr—Thr—Asp—Leu—Ser—Leu—Ser—His—Ser—Pro—Gly

—Lys.

4. A process for producing a chimeric immunoglobulin gamma heavy chain, wherein said immunoglobulin gamma heavy chain has a variable region of a mouse immunoglobulin and a constant region from a canine immunoglobulin gamma constant region, which comprises:

inserting the DNA of claim 2 into a vector for expressing said DNA, transforming a mammalian cell with said expression vector so produced, culturing said transformed cell, and recovering said immunoglobulin gamma heavy chain produced by said transformed cell.

5. A process for producing a chimeric immunoglobulin gamma heavy chain, wherein said immunoglobulin gamma heavy chain has a variable region of a mouse immunoglobulin and a constant region from a canine immunoglobulin gamma constant region, which comprises:

inserting the DNA of claim 3, into a vector comprising a first DNA molecule encoding a variable region of a mouse immunoglobulin and a second DNA molecule according to claim 3, wherein said second DNA molecule is operatively linked to the 3' end of said first DNA molecule, into a vector for expressing said DNA for expressing said DNA, transforming a mammalian cell with the expression vector so produced, culturing said transformed cell, and recovering said immunoglobulin gamma heavy chain produced by said transformed cell.

6. A recombinant DNA molecule coding for a mouse-dog chimeric antibody H chain which comprises the gene fragment as set forth in claim 3 which codes for an amino acid sequence of a constant region of canine immunoglobulin gamma chain and a gene fragment coding for an amino acid sequence of a variable region of mouse immunoglobulin H chain wherein the former gene fragment is linked to the 3' site of the latter gene fragment.

* * * * *